(12) United States Patent
Goebel et al.

(10) Patent No.: US 7,262,209 B2
(45) Date of Patent: Aug. 28, 2007

(54) CARBONYLOXY-CYANOMETHYL COMPOUNDS AS ANTIPARASITIC AGENTS

(75) Inventors: Thomas Goebel, Lorrach (DE); Pierre Ducray, Village-Neuf (FR)

(73) Assignee: Novartis Animal Health US, Inc., Greensboro, NC (US)

( * ) Notice: Subject to any disclaimer, the term of this patent is extended or adjusted under 35 U.S.C. 154(b) by 87 days.

(21) Appl. No.: 10/487,167

(22) PCT Filed: Oct. 2, 2002

(86) PCT No.: PCT/EP02/11087

§ 371 (c)(1),
(2), (4) Date: Feb. 17, 2004

(87) PCT Pub. No.: WO03/031393

PCT Pub. Date: Apr. 17, 2003

(65) Prior Publication Data

US 2004/0236137 A1 Nov. 25, 2004

(30) Foreign Application Priority Data

Oct. 4, 2001 (CH) ..................................... 1829/01

(51) Int. Cl.
*A01N 47/10* (2006.01)
*A01N 43/40* (2006.01)
*C07D 213/00* (2006.01)
*C09C 69/96* (2006.01)
*C09C 229/00* (2006.01)

(52) U.S. Cl. ...................... 514/332; 514/335; 514/344; 514/345; 514/351; 514/352; 514/357; 514/478; 514/479; 514/487; 546/261; 546/265; 546/286; 546/288; 546/290; 546/304; 546/309; 546/330; 558/270; 558/271; 558/273; 560/24; 560/26; 560/47

(58) Field of Classification Search ................ 558/273, 558/270, 271; 560/24, 45, 47, 49, 61, 62; 546/290, 360, 361, 261, 265, 286, 289, 304, 546/309, 330; 514/332, 335, 344, 345, 351, 514/362, 357, 478, 479, 487
See application file for complete search history.

(56) References Cited

U.S. PATENT DOCUMENTS 4,833,163 A 5/1989 Martel et al.

FOREIGN PATENT DOCUMENTS

| CA | 2052894 | 11/1992 |
|---|---|---|
| EP | 0 480 258 | 9/1991 |
| EP | 0 630 890 | 12/1994 |
| EP | 0 953 565 | 11/1999 |

*Primary Examiner*—Thomas McKenzie
*Assistant Examiner*—Raymond Covington
(74) *Attorney, Agent, or Firm*—E. Jay Wilusz

(57) ABSTRACT

The invention relates to compounds of the general formula $$Ar_1 \overset{X}{\underset{O}{-}} \overset{}{-} O \overset{R_4}{\underset{CN}{-}} \overset{R_5}{\underset{R_6}{-}} (C)_a - W - (C)_b \overset{R_7}{\underset{R_8}{-}} Ar_2,$$

I wherein $Ar_1$, $Ar_2$, $R_4$, $R_5$, $R_6$, $R_7$, $R_8$, W, X, a and b have the significances given in the specification, and optionally the enantiomers thereof. The active ingredients have advantageous pesticidal properties. They are especially suitable for controlling parasites on warm-blooded animals.

39 Claims, No Drawings

CARBONYLOXY-CYANOMETHYL COMPOUNDS AS ANTIPARASITIC AGENTS

This application is a National Phase Application under § 371 of International Application No. PCT/EP02/11087 filed on Oct. 2. 2002.

The present invention relates to new carbonyloxy-cyanomethyl compounds of formula

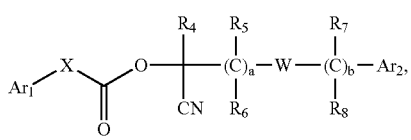

wherein

Ar$_1$ and Ar$_2$, independently of one another, signify unsubstituted phenyl or phenyl which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_2$–C$_6$-alkenyl, halo-C$_2$–C$_6$-alkenyl, C$_2$–C$_6$-alkinyl, C$_3$–C$_6$-cycloalkyl, C$_2$–C$_6$-alkenyloxy, halo-C$_2$–C$_6$-alkenyloxy, C$_1$–C$_6$-alkylthio, halo-C$_1$–C$_6$-alkylthio, C$_1$–C$_6$-alkylsulfonyloxy, halo-C$_1$–C$_6$-alkylsulfonyloxy, C$_1$–C$_6$-alkylsulfinyl, halo-C$_1$–C$_6$-alkylsulfinyl, C$_1$–C$_6$-alkylsulfonyl, halo-C$_1$–C$_6$-alkylsulfonyl, C$_2$–C$_6$-alkenylthio, halo-C$_2$–C$_6$-alkenylthio, C$_2$–C$_6$-alkenylsulfinyl, halo-C$_2$–C$_6$-alkenylsulfinyl, C$_2$–C$_6$-alkenylsulfonyl, halo-C$_2$–C$_6$-alkenylsulfonyl, C$_1$–C$_6$-alkylamino, di-C$_1$–C$_6$-alkylamino, C$_1$–C$_6$-alkylsulfonylamino, halo-C$_1$–C$_6$-alkylsulfonylamino, C$_1$–C$_6$-alkylcarbonyl, halo-C$_1$–C$_6$-alkylcarbonyl, C$_1$–C$_6$-alkoxycarbonyl, C$_1$–C$_6$-alkylaminocarbonyl, di-C$_1$–C$_6$-alkylaminocarbonyl, unsubstituted phenylamino or phenylamino which is substituted once or many times, unsubstituted phenylcarbonyl or phenylcarbonyl which is substituted once or many times; unsubstituted phenyl or phenyl which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkylthio, halo-C$_1$–C$_6$-alkyylthio, C$_1$–C$_6$-alkylsulfinyl, halo-C$_1$–C$_6$-alkylsulfinyl, C$_1$–C$_6$-alkylsulfonyl and halo-C$_1$–C$_6$-alkylsulfonyl; substituted phenoxy or phenoxy which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_1$–C$_6$-alkylsulfonyl and halo-C$_1$–C$_6$-alkylsulfonyl; unsubstituted phenylacetylenyl or phenylacetylenyl which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_1$–C$_6$-alkylsulfonyl and halo-C$_1$–C$_6$-alkylsulfonyl; and unsubstituted pyridyloxy or pyridyloxy which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_1$–C$_6$-alkylsulfonyl and halo-C$_1$–C$_6$-alkylsulfonyl;

unsubstituted heteroaryl or heteroaryl which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_2$–C$_6$-alkenyloxy, halo-C$_2$–C$_6$-alkenyloxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_2$–C$_6$-alkenylthio, halo-C$_2$–C$_6$-alkenylthio, C$_2$–C$_6$-alkenylsulfinyl, halo-C$_2$–C$_6$-alkenylsulfinyl, C$_1$–C$_6$-alkylsulfonyl and halo-C$_1$–C$_6$-alkylsulfonyl, C$_2$–C$_6$-alkenylsulfonyl, halo-C$_2$–C$_6$-alkenylsulfonyl, C$_1$–C$_6$-alkylamino and di-C$_1$–C$_6$-alkylamino; or unsubstituted naphthyl or quinolyl, or naphthyl or quinolyl which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_2$–C$_6$-alkenyloxy, halo-C$_2$–C$_6$-alkenyloxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_2$–C$_6$-alkenylthio, halo-C$_2$–C$_6$-alkenylthio, C$_2$–C$_6$-alkenylsulfinyl, halo-C$_2$–C$_6$-alkenylsulfinyl, C$_1$–C$_6$-alkylsulfonyl and halo-C$_1$–C$_6$-alkylsulfonyl, C$_2$–C$_6$-alkenylsulfonyl, halo-C$_2$–C$_6$-alkenylsulfonyl, C$_1$–C$_6$-alkylamino and di-C$_1$–C$_6$-alkylamino;

R$_4$, R$_5$, R$_6$, R$_7$ and R$_8$ are either, independently of one another, hydrogen, halogen, unsubstituted C$_1$–C$_6$-alkyl or C$_1$–C$_6$-alkyl which is substituted once or many times, unsubstituted C$_2$–C$_6$-alkenyl or C$_2$–C$_6$-alkenyl which is substituted once or many times, unsubstituted C$_2$–C$_6$-alkinyl or C$_2$–C$_6$-alkinyl which is substituted once or many times, whereby the substituents may each be independent of one another and are selected from the group consisting of halogen, C$_1$–C$_6$-alkoxy and halo-C$_1$–C$_6$-alkoxy; C$_3$–C$_6$-cycloalkyl, whereby the substituents may be independent of one another and are selected from the group consisting of halogen and C$_1$–C$_6$-alkyl; unsubstituted phenyl or phenyl which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_1$–C$_6$-alkylsulfonyl, halo-C$_1$–C$_6$-alkylsulfonyl, C$_1$–C$_6$-alkylamino or di-C$_1$–C$_6$-alkylamino;

or R$_4$ and R$_5$ together signify C$_2$–C$_6$-alkylene;

W signifies O, S, S(O$_2$) or N(R$_9$);

R$_9$ signifies hydrogen or C$_1$–C$_6$-alkyl;

X signifies O, S or N(R$_{10}$);

R$_{10}$ signifies hydrogen, C$_1$–C$_6$-alkyl, halo-C$_1$–C$_6$-alkyl, allyl or C$_1$–C$_6$-alkoxymethyl;

a signifies 1, 2, 3 or 4; and b signifies 0, 1, 2, 3 or 4.

In literature, various compounds have been proposed as active ingredients having anthelminthic properties in pesticides for use on domestic animals and productive livestock. The biological properties of these known compounds, however, are not fully satisfactory in the field of pest control, which is why there is a need to produce further compounds with pesticidal properties, especially for the control of endoparasites; this problem is solved according to the invention with the development of the present compounds I.

Alkyl—as a group per se and as structural element of other groups and compounds such as halogen-alkyl, alkylamino, alkoxy, alkylthio, alkylsulfinyl and alkylsulfonyl— is, in each case with due consideration of the specific number of carbon atoms in the group or compound in question, either straight-chained, i.e. methyl, ethyl, propyl, butyl, pentyl, hexyl, heptyl or octyl, or branched, e.g. isopropyl, isobutyl, sec.-butyl, tert.-butyl, isopentyl, neopentyl or isohexyl.

Cycloalkyl—as a group per se and as structural element of other groups and compounds such as halocycloalkyl, cycloalkoxy and cycloalkylthio,—is, in each case with due consideration of the specific number of carbon atoms in the group or compound in question, cyclopropyl, cyclobutyl, cyclopentyl, cyclohexyl, cycloheptyl or cyclooctyl.

Alkenyl—as a group per se and as structural element of other groups and compounds—is, in each case with due consideration of the specific number of carbon atoms in the group or compound in question and of the conjugated or isolated double bonds—either straight-chained, e.g. allyl, 2-butenyl, 3-pentenyl, 1-hexenyl, 1-heptenyl, 1,3-hexadienyl or 1,3-octadienyl, or branched, e.g. isopropenyl, isobutenyl, isoprenyl, tert.-pentenyl, isohexenyl, isoheptenyl or isooctenyl.

Alkinyl—as a group per se and as structural element of other groups and compounds—is, in each case with due consideration of the specific number of carbon atoms in the group or compound in question and of the conjugated or isolated double bonds—either straight-chained, e.g. propargyl, 2-butinyl, 3-pentinyl, 1-hexinyl, 1-heptinyl, 3-hexen-1-inyl or 1,5-heptadien-3-inyl, or branched, e.g. 3-methylbut-1-inyl, 4-ethylpent-1-inyl, 4-methylhex-2-inyl or 2-methylhept-3-inyl.

Heteroaryl is pyridyl, thienyl, furanyl, pyrryl, benzothienyl, benzofuranyl, indolyl or indazolyl, preferably pyridyl or thienyl, especially pyridyl.

As a rule, halogen signifies fluorine, chlorine, bromine or iodine. The same applies to halogen in combination with other significances, such as halogenalkyl or halogenphenyl.

Halogen-substituted carbon-containing groups and compounds may be partially halogenated or perhalogenated, whereby in the case of multiple halogenation, the halogen substituents may be identical or different. Examples of halogen-alkyl—as a group per se and as structural element of other groups and compounds such as halogen-alkoxy or halogen-alkylthio,—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers substituted once to eleven times by fluorine, chlorine and/or bromine, such as $CF(CF_3)(CHF)_2CF_3$ or $CH_2(CF_2)_3CF_3$; and hexyl or one of its isomers substituted once to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Alkoxy groups preferably have a chain length of 1 to 6 carbon atoms. Alkoxy is for example methoxy, ethoxy, propoxy, isopropoxy, n-butoxy, isobutoxy, sec.-butoxy and tert.-butoxy, as well as the isomers pentyloxy and hexyloxy; preferably methoxy and ethoxy. Halogenalkoxy groups preferably have a chain length of 1 to 6 carbon atoms. Halogenalkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2, 2-trichloroethoxy; preferably difluoromethoxy, 2-chloroethoxy and trifluoromethoxy.

Preferred embodiments within the scope of the invention are:

(1) A compound of formula I, wherein $Ar_1$ and $Ar_2$, independently of one another, signify unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_2$–$C_6$-alkenyl, halo-$C_2$–$C_6$-alkenyl, $C_2$–$C_6$-alkinyl, $C_3$–$C_6$-cycloalkyl, $C_2$–$C_6$-alkenyloxy, halo-$C_2$–$C_6$-alkenyloxy, $C_1$–$C_6$-alkylthio, halo-$C_1$–$C_6$-alkylthio, $C_1$–$C_6$-alkylamino, di-$C_1$–$C_6$-alkylamino, $C_1$–$C_6$-alkylcarbonyl, halo-$C_1$–$C_6$-alkylcarbonyl, $C_1$–$C_6$-alkoxycarbonyl, $C_1$–$C_6$-alkylaminocarbonyl and di-$C_1$–$C_6$-alkylaminocarbonyl;

heteroaryl that is either unsubstituted or substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_2$–$C_6$-alkenyloxy, halo-$C_2$–$C_6$-alkenyloxy, $C_1$–$C_6$-alkylthio, halo-$C_1$–$C_6$-alkylthio, $C_1$–$C_6$-alkylamino and di-$C_1$–$C_6$-alkylamino; or naphthyl that is either unsubstituted or substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_2$–$C_6$-alkenyloxy, halo-$C_2$–$C_6$-alkenyloxy, $C_1$–$C_6$-alkylthio, halo-$C_1$–$C_6$-alkylthio, $C_1$–$C_6$-alkylamino and di-$C_1$–$C_6$-alkylamino;

especially phenyl that is, independently of one another, either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy, halo-$C_1$–$C_6$-alkoxy, $C_3$–$C_6$-cycloalkyl, $C_1$–$C_6$-alkylthio, halo-$C_1$–$C_6$-alkylthio, $C_1$–$C_6$-alkylcarbonyl, halo-$C_1$–$C_6$-alkylcarbonyl, $C_1$–$C_6$-alkoxycarbonyl, $C_1$–$C_6$-alkylaminocarbonyl and di-$C_1$–$C_6$-alkylaminocarbonyl;

heteroaryl that is either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkylamino and di-$C_1$–$C_6$-alkylamino; or naphthyl that is either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkylamino and di-$C_1$–$C_6$-alkylamino;

most particularly phenyl that is, independently of one another, either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy and halo-$C_1$–$C_6$-alkoxy; or heteroaryl that is either unsubstituted or substituted once or many times, whereby the substituents may be independent of one another and are selected from the group consisting of halogen, $C_1$–$C_6$-alkyl and halo-$C_1$–$C_6$-alkyl;

(2) A compound of formula I, wherein $R_4$, $R_5$, $R_6$, $R_7$ and $R_8$ are, independently of one another, hydrogen, halogen, unsubstituted $C_1$–$C_6$-alkyl or $C_1$–$C_6$-alkyl which is substituted once or many times, unsubstituted $C_2$–$C_6$-alkenyl or $C_2$–$C_6$-alkenyl which is substituted once or many times, unsubstituted $C_2$–$C_6$-alkinyl or $C_2$–$C_6$-alkinyl which is substituted once or many times, whereby the substituents may each be independent of one another and are selected from the group consisting of halogen, $C_1$–$C_6$-alkoxy and halo-$C_1$–$C_6$-alkoxy; unsubstituted $C_3$–$C_6$-Cycloalkyl or $C_3$–$C_6$-cycloalkyl which is substituted once or many times, whereby the substituents may be independent of one another and are selected from the group consisting of halogen and $C_1$–$C_6$-alkyl; or unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkylsulfonyl, halo-$C_1$–$C_6$-alkylsulfonyl, $C_1$–$C_6$-alkylamino or di-$C_1$–$C_6$-alkylamino;

especially, independently of one another, hydrogen, halogen, unsubstituted $C_1$–$C_6$-alkyl or $C_1$–$C_6$-alkyl which is substituted once or many times, unsubstituted $C_2$–$C_6$-alkenyl or $C_2$–$C_6$-alkenyl which is substituted once or many times, unsubstituted $C_2$–$C_6$-alkinyl or $C_2$–$C_6$-alkinyl which is substituted once or many times, whereby the substituents may each be independent of one another and are selected from the group consisting of halogen and $C_1$–$C_6$-alkoxy; unsubstituted $C_3$–$C_6$-cycloalkyl or $C_3$–$C_6$-cycloalkyl which is substituted once or many times, whereby the substituents may be independent of one another and are selected from the group consisting of halogen and $C_1$–$C_4$-alkyl; or unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy or halo-$C_1$–$C_6$-alkoxy;

especially, independently of one another, hydrogen, halogen, $C_1$–$C_4$-alkyl or halo-$C_1$–$C_4$-alkyl;

(3) A compound of formula I, wherein W is O, S or $N(R_9)$; especially O or S;
particularly O;

(4) A compound of formula I, wherein $R_9$ signifies hydrogen or $C_1$–$R_4$-alkyl;
especially hydrogen or $C_1$–$C_2$-alkyl;
most particularly hydrogen;

(5) A compound of formula I, wherein X is O or $N(R_{10})$; especially $N(R_{10})$;

(6) A compound of formula I, wherein $R_{10}$ is hydrogen, $C_1$–$C_4$-alkyl or halo-$C_1$–$C_4$-alkyl;
especially hydrogen or $C_1$–$C_4$-alkyl;
most particularly hydrogen;

(7) A compound of formula I, wherein a signifies 1, 2 or 3;
especially 1 or 2;
most particularly 1;

(8) A compound of formula I, wherein b is 0, 1, 2 or 3;
especially 0 or 1;
most particularly 0;

(9) A compound of formula I, wherein $Ar_1$ and $Ar_2$, independently of one another, signify unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_2$–$C_6$-alkenyl, halo-$C_2$–$C_6$-alkenyl, $C_2$–$C_6$-alkinyl, $C_3$–$C_6$-cycloalkyl, $C_2$–$C_6$-alkenyloxy, halo-$C_2$–$C_6$-alkenyloxy, $C_1$–$C_6$-alkylthio, halo-$C_1$–$C_6$-alkylthio, $C_1$–$C_6$-alkylamino, di-$C_1$–$C_6$-alkylamino, $C_1$–$C_6$-alkylcarbonyl, halo-$C_1$–$C_6$-alkylcarbonyl, $C_1$–$C_6$-alkoxycarbonyl, $C_1$–$C_6$-alkylaminocarbonyl and di-$C_1$–$C_6$-alkylaminocarbonyl;

heteroaryl that is either unsubstituted or substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_2$–$C_6$-alkenyloxy, halo-$C_2$–$C_6$-alkenyloxy, $C_1$–$C_6$-alkylthio, halo-$C_1$–$C_6$-alkylthio, $C_1$–$C_6$-alkylamino and di-$C_1$–$C_6$-alkylamino; or naphthyl that is either unsubstituted or substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_2$–$C_6$-alkenyloxy, halo-$C_2$–$C_6$-alkenyloxy, $C_1$–$C_6$-alkylthio, halo-$C_1$–$C_6$-alkylthio, $C_1$–$C_6$-alkylamino and di-$C_1$–$C_6$-alkylamino;

$R_4$, $R_5$, $R_6$, $R_7$ and $R_8$ are, independently of one another, hydrogen, halogen, unsubstituted $C_1$–$C_6$-alkyl or $C_1$–$C_6$-alkyl which is substituted once or many times, unsubstituted $C_2$–$C_6$-alkenyl or $C_2$–$C_6$-alkenyl which is substituted once or many times, unsubstituted $C_2$–$C_6$-alkinyl or $C_2$–$C_6$-alkinyl which is substituted once or many times, whereby the substituents may each be independent of one another and are selected from the group consisting of halogen and $C_1$–$C_6$-alkoxy; unsubstituted $C_3$–$C_6$-cycloalkyl or $C_3$–$C_6$-cycloalkyl which is substituted once or many times, whereby the substituents may be independent of one another and are selected from the group consisting of halogen and $C_1$–$C_6$-alkyl; or unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkylsulfonyl, halo-$C_1$–$C_6$-alkylsulfonyl, $C_1$–$C_6$-alkylamino or di-$C_1$–$C_6$-alkylamino;

W signifies O, S or $N(R_9)$;
$R_9$ signifies hydrogen or $C_1$–$C_4$-alkyl;
X signifies O or $N(R_{10})$;
$R_{10}$ signifies hydrogen, $C_1$–$C_4$-alkyl or halo-$C_1$–$C_4$-alkyl;
a signifies 1, 2 or 3;
and b signifies 0, 1, 2 or 3.

(10) A compound of formula I, wherein $Ar_1$ and $Ar_2$, independently of one another, signify phenyl that is either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy, halo-$C_1$–$C_6$-alkoxy, $C_3$–$C_6$-cycloalkyl, $C_1$–$C_6$-alkylthio, halo-$C_1$–$C_6$-alkylthio, $C_1$–$C_6$-alkylcarbonyl, halo-$C_1$–$C_6$-alkylcarbonyl, $C_1$–$C_6$-alkoxycarbonyl, $C_1$–$C_6$-alkylaminocarbonyl and di-$C_1$–$C_6$-alkylaminocarbonyl;

heteroaryl that is either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkylamino and di-$C_1$–$C_6$-alkylamino; or naphthyl that is either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkylamino and di-$C_1$–$C_6$-alkylamino;

$R_4$, $R_5$, $R_6$, $R_7$ and $R_8$ are, independently of one another, hydrogen, halogen, unsubstituted $C_1$–$C_6$-alkyl or $C_1$–$C_6$-alkyl which is substituted once or many times, unsubstituted $C_2$–$C_6$-alkenyl or $C_2$–$C_6$-alkenyl which is substituted once or many times, unsubstituted $C_2$–$C_6$-alkinyl or $C_2$–$C_6$-alkinyl which is substituted once or many times, whereby the substituents may each be independent of one another and are selected from the group consisting of halogen and $C_1$–$C_6$-alkoxy; unsubstituted $C_3$–$C_6$-cycloalkyl or $C_3$–$C_6$-cycloalkyl which is substituted once or many times, whereby the substituents may be independent of one another and are selected from the group consisting of halogen and $C_1$–$C_4$-alkyl; or unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy or halo-$C_1$–$C_6$-alkoxy;

W is O or S;
$R_9$ signifies hydrogen or $C_1$–$C_2$-alkyl;
X signifies $N(R_{10})$;
$R_{10}$ signifies hydrogen or $C_1$–$C_4$-alkyl;
a signifies 1 or 2;
and b signifies 0 or 1.

(11) A compound of formula I, wherein $Ar_1$ and $Ar_2$, independently of one another, signify phenyl that is either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy and halo-$C_1$–$C_6$-alkoxy; or heteroaryl that is either unsubstituted or substituted once or many times, whereby the substituents may be independent of one another and are selected from the group consisting of halogen, $C_1$–$C_6$-alkyl and halo-$C_1$–$C_6$-alkyl;

$R_4$, $R_5$, $R_6$, $R_7$ and $R_8$, independently of one another, signify hydrogen, halogen, $C_1$–$C_4$-alkyl or halo-$C_1$–$C_4$-alkyl;
W signifies O;
$R_9$ signifies hydrogen;
X signifies $N(R_{10})$;
$R_{10}$ signifies hydrogen;
a signifies 1; and
b is 1.

Within the context of the invention, particular preference is given to the compounds of formula I listed in the tables, and most particularly those named in the synthesis examples.

A further object of the invention is the process for the preparation of the compounds of formula I, respectively in free form or in salt form, for example characterised in that a compound of formula

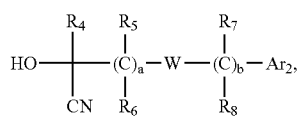

II which is known or may be produced analogously to corresponding known compounds, and wherein $R_4$, $R_5$, $R_6$, $R_7$, $R_8$, $Ar_2$, W, a and b are defined as given for formula I, a) in order to produce a compound of formula I, wherein X is defined as given for formula I with the exception of NH, is reacted with a compound of formula

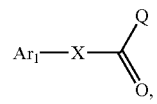

III which is known or may be produced analogously to corresponding known compounds, and wherein $Ar_1$ and X are defined as given for formula I and Q is a leaving group, or b) in order to produce a compound of formula I, wherein X is NH and n is 1, is reacted with a compound of formula

VI, which is known or may be produced analogously to corresponding known compounds, and wherein $Ar_1$ is defined as given for formula I, optionally in the presence of a basic catalyst; and if desired, a compound of formula I obtainable according to the method or in another way, respectively in free form or in salt form, is converted into another compound of formula I, a mixture of isomers obtainable according to the method is separated and the desired isomer isolated and/or a free compound of formula I obtainable according to the method is converted into a salt or a salt of an compound of formula I obtainable according to the method is converted into the free compound of formula I or into another salt.

What has been stated above for salts of compounds I also applies analogously to salts of the starting materials listed hereinabove and hereinbelow.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxane; ketones such as acetone, methyl ethyl ketone or methyl isobutyl ketone; amides such as N,N-dimethylformamide, N,N-diethyl-formamide, N,N-dimethylacetamide, N-methylpyrrolidone or hexamethylphosphoric acid triamide; nitrites such as acetonitrile or propionitrile; and sulfoxides, such as dimethyl sulfoxide.

Preferred leaving groups Q are halogens, especially chlorine.

Suitable bases for facilitating the reaction are e.g. alkali metal or alkaline earth metal hydroxides, hydrides, amides, alkanolates, acetates, carbonates, dialkylamides or alkylsilyl-amides; alkylamines, alkylenediamines, optionally N-alkylated, optionally unsaturated, cyclo-alkylamines, basic heterocycles, ammonium hydroxides, as well as carbocyclic amines. Those which may be mentioned by way of example are sodium hydroxide, hydride, amide, methanolate, acetate, carbonate, potassium tert.-butanolate, hydroxide, carbonate, hydride, lithium diisopropylamide, potassium bis(trimethylsilyl)-amide, calcium hydride, triethylamine, diisopropylethylamine, triethylenediamine, cyclohexylamine, N-cyclohexyl-N,N-dimethyl-amine, N,N-diethylaniline, pyridine, 4-(N,N-dimethylamino)pyridine, quinuclidine, N-methyl-morpholine, benzyltrimethylammonium hydroxide, as well as 1,5-diazabicyclo[5.4.0]undec-5-ene (DBU).

The reaction advantageously takes place in a temperature range of ca. 0° C. to ca. 150° C., preferably from ca. 20° C. to ca. 100° C.

Salts of compounds I may be produced in known manner. Acid addition salts, for example, are obtainable from compounds I by treating with a suitable acid or a suitable ion exchange reagent, and salts with bases are obtainable by treating with a suitable base or a suitable ion exchange reagent Salts of compounds I can be converted into the free compounds I by the usual means, acid addition salts e.g. by treating with a suitable basic composition or with a suitable ion exchange reagent, and salts with bases e.g. by treating with a suitable acid or a suitable ion exchange reagent.

Salts of compounds I can be converted into other salts of compounds I in a known manner; acid addition salts can be converted for example into other acid addition salts, e.g. by treating a salt of an inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds I with salt-forming characteristics can be obtained in free form or in the form of salts.

Compounds I can also be obtained in the form of their hydrates and/or also can include other solvents, used for example where necessary for the crystallisation of compounds present in solid form.

The compounds I may be optionally present as optical and/or geometric isomers or as a mixture thereof. The invention relates both to the pure isomers and to all possible isomeric mixtures, and is hereinbefore and hereinafter understood as doing so, even if stereochemical details are not specifically mentioned in every case.

Diastereoisomeric mixtures of compounds 1, which are obtainable by the process or in another way, may be separated in known manner, on the basis of the physical-chemical differences in their components, into the pure diastereoisomers, for example by fractional crystallisation, distillation and/or chromatography.

Splitting of mixtures of enantiomers that are obtainable accordingly may be achieved by known methods, for example by recrystallisation from an optically active solvent, by chromatography on chiral adsorbents, e.g. high-pressure liquid chromatography (HPLC) on acetyl cellulose, with the assistance of appropriate micro-organisms, by cleavage with specific immobilised enzymes, through the formation of inclusion compounds, e.g. using chiral crown ethers, whereby only one enantiomer is complexed.

According to the invention, apart from separation of corresponding isomer mixtures, generally known methods of diastereoselective or enantioselective synthesis can also be applied to obtain pure diastereoisomers or enantiomers, e.g. by carrying out the method of the invention using educts with correspondingly suitable stereochemistry.

It is advantageous to isolate or synthesise the biologically more active isomer, e.g. enantiomer, provided that the individual components have differing biological efficacy.

In the method of the present invention, the starting materials and intermediates used are preferably those that lead to the compounds I described at the beginning as being especially useful.

The invention relates in particular to the preparation methods described in the examples.

Starting materials and intermediates, which are new and are used according to the invention for the preparation of compounds I, as well as their usage and process for the preparation thereof, similarly form an object of the invention.

The compounds I according to the invention are notable for their broad activity spectrum and are valuable active ingredients for use in pest control, including in particular the control of endoparasites on animals, whilst being well-tolerated by warm-blooded animals, fish and plants, In the context of the present invention, ectoparasites are understood to be in particular insects, mites and ticks. These include insects of the order: *Lepidoptera*, *Coleoptera*, *Homoptera*, *Heteroptera*, *Diptera*, *Thysanoptera*, *Orthoptera*, *Anoplura*, *Siphonaptera*, *Mallophaga*, *Thysanura*, *Isoptera*, *Psocoptera* and *Hymenoptera*. However, the ectoparasites which may be mentioned in particular are those which trouble humans or animals and carry pathogens, for example flies such as *Musca domestica*, *Musca vetustissima*, *Musca autumnalis*, *Fannia canicularis*, *Sarcophaga camaria*, *Lucilia cuprina*, *Hypoderrna bovis*, *Hypoderrna lineatum*, *Chrysomyia chloropyga*, *Dermatobia hominis*, *Cochliomyia hominivorax*, *Gasterophilus intestinalis*, *Oestrus ovis*, *Stomoxys calcitrans*, *Haematobia irritans* and midges (*Nematocera*), such as *Culicidae*, *Simuliidae*, *Psychodidae*, but also blood-sucking parasites, for example fleas, such as *Ctenocephalides felis* and *Ctenocephalides canis* (cat and dog fleas), *Xenopsylla cheopis*, *Pulex irritans*, *Dermatophilus penetrans*, lice, such as *Damalina ovis*, *Pediculus humanis*, biting flies and horse-flies (*Tabanidae*), *Haematopota* spp. such as *Haematopota pluvialis*, *Tabanidea* spp. such as *Tabanus nigrovittatus*, *Chrysopsinae* spp. such as *Chrysops caecutiens*, tsetse flies, such as species of *Glossinia*, biting insects, particularly cockroaches, such as *Blatella germanica*, *Blatta orientalis*, *Periplaneta americana*, mites, such as *Dermanyssus gallinae*, *Sarcoptes scabiei*, *Psoroptes ovis* and *Psorergates* spp. and last but not least ticks. The latter belong to the order *Acarina*. Known representatives of ticks are, for example, *Boophilus*, *Amblyomma*, *Anocentor*, *Dermacentor*, *Haemaphysalis*, *Hyalomma*, *Ixodes*, *Rhipicentor*, *Margaropus*, *Rhipicephalus*, *Argas*, *Otobius* and *Ornithodoros* and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

The compounds I according to the invention are also active against all or individual development stages of animal pests showing normal sensitivity, as well as those showing resistance, such as insects and members of the order *Acarina*. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds I can also be used against hygiene pests, especially of the order *Diptera* of the families *Sarcophagidae, Anophilidae* and *Culicidae*; the orders *Orthoptera, Dictyoptera* (e.g. the family *Blattidae*) and *Hymenoptera* (e.g. the family *Formicidae*).

The compounds of formula I are also effective against plant nematodes of the species *Meloidogyne, Heterodera, Pratylenchus, Ditylenchus, Radopholus, Rizoglyphus* etc.

In particular, the compounds are effective against helminths, in which the endoparasitic nematodes and trematodes may be the cause of serious diseases of mammals and poultry, e.g. sheep, pigs, goats, cattle, horses, donkeys, dogs, cats, guinea-pigs and exotic birds. Typical nematodes of this indication are: *Haemonchus, Trichostrongylus, Ostertagia, Nematodirus, Cooperia, Ascaris, Bunostonum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. The trematodes include, in particular, the family of *Fasciolideae*, especially *Fasciola hepatica*. The particular advantage of the compounds of formula I is their efficacy against those parasites that are resistant towards active ingredients based on benzimidazole.

Certain pests of the species *Nematodirus, Cooperia* and *Oesophagostonum* infest the intestinal tract of the host animal, while others of the species *Haemonchus* and *Ostertagia* are parasitic in the stomach and those of the species *Dictyocaulus* are parasitic in the lung tissue. Parasites of the families *Filariidae* and *Setariidae* may be found in the internal cell tissue and in the organs, e.g. the heart, the blood vessels, the lymph vessels and the subcutaneous tissue. A particularly notable parasite is the heartworm of the dog, *Dirofilaria immitis*. The compounds of formula I are highly effective against these parasites.

The pests which may be controlled by the compounds of formula I also include those from the class of *Cestoda* (tapeworms), e.g. the families *Mesocestoidae*, especially of the genus *Mesocestoides*, in particular *M. lineatus; Dilepidide*, especially *Dipylidium caninum, Joyeuxiella* spp., in particular *Joyeuxiella pasquali*, and *Diplopylidium* spp., and *Taeniidae*, especially *Taenia pisiformis, Taenia cervi, Taenia ovis, Taneia hydatigena, Taenia multiceps, Taenia taeniaeformis, Taenia serialis*, and *Echinocuccus* spp., most preferably *Taneia hydatigena, Taenia ovis, Taenia multiceps, Taenia serialis; Echinocuccus granulosus* and *Echinococcus granulosus* and *Echinococcus multilocularis*, as well as *Multiceps multiceps*.

Most particularly, *Taenia hydatigena, T. pisiformis, T. ovis, T. taeniaeformis, Multiceps multiceps, Joyeuxiella pasquali, Dipylidium caninum, Mesocestoides* spp., *Echinococcus granulosus* and *E. multilocularis* are controlled on or in dogs and cats simultaneously with *Dirofilaria immitis, Ancylostoma* ssp., *Toxocara* ssp. and/or *Trichuris vulpis*.

Furthermore, the compounds of formula I are suitable for the control of human pathogenic parasites. Of these, typical representatives that appear in the digestive tract are those of the species *Ancylostoma, Necator, Ascaris, Strongyloides, Trichinella, Capillaria, Trichuris* and *Enterobius*. The compounds of the present invention are also effective against parasites of the species *Wuchereria, Brugia, Onchocerca* and *Loa* from the family of *Filariidae*, which appear in the blood, in the tissue and in various organs, and also against *Dracunculus* and parasites of the species *Strongyloides* and *Trichinella*, which infect the gastrointestinal tract in particular.

In addition, the compounds of formula I are also effective against harmful and pathogenic fungi on plants, as well as on humans and animals.

The good pesticidal activity of the compounds of formula I according to the invention corresponds to a mortality rate of at least 50–60% of the pests mentioned. The compounds of formula I are preferably employed in unmodified form or preferably together with the adjuvants conventionally used in the art of formulation and may therefore be processed in a known manner to give, for example, emulsifiable concentrates, directly dilutable solutions, dilute emulsions, soluble powders, granules or microencapsulations in polymeric substances. As with the compositions, the methods of application are selected in accordance with the intended objectives and the prevailing circumstances.

The formulation, i.e. the agents, preparations or compositions containing the active ingredient of formula I, or combinations of these active ingredients with other active ingredients, and optionally a solid or liquid adjuvant, are produced in a manner known per se, for example by intimately mixing and/or grinding the active ingredients with spreading compositions, for example with solvents, solid carriers, and optionally surface-active compounds (surfactants).

The solvents in question may be: alcohols, such as ethanol, propanol or butanol, and glycols and their ethers and esters, such as propylene glycol, dipropylene glycol ether, ethylene glycol, ethylene glycol monomethyl or -ethyl ether, ketones, such as cyclohexanone, isophorone or diacetanol alcohol, strong polar solvents, such as N-methyl-2-pyrrolidone, dimethyl sulfoxide or dimethylformamide, or water, vegetable oils, such as rape, castor, coconut, or soybean oil, and also, if appropriate, silicone oils.

Preferred application forms for usage on warm-blooded animals in the control of helminths include solutions, emulsions, suspensions (drenches), food additives, powders, tablets including effervescent tablets, boli, capsules, microcapsules and pour-on formulations, whereby the physiological compatibility of the formulation excipients must be taken into consideration.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), glidants and disintegrants.

If the anthelminthics are present in the form of feed concentrates, then the carriers used are e.g. performance feeds, feed grain or protein concentrates. Such feed concentrates or compositions may contain, apart from the active ingredients, also additives, vitamins, antibiotics, chemotherapeutics or other pesticides, primarily bacteriostats, fungistats, coccidiostats, or even hormone preparations, substances having anabolic action or substances which promote growth, which affect the quality of meat of animals for slaughter or which are beneficial to the organism in another way. If the compositions or the active ingredients of formula I contained therein are added directly to feed or to the drinking troughs, then the formulated feed or drink contains the active ingredients preferably in a concentration of ca. 0.0005 to 0.02% by weight (5–200 ppm).

The compounds of formula I according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. Since the compounds of formula I are adulticides, i.e. since they are effective in particular against the adult stage of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance.

Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula I.

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers.

Non-limitative examples of suitable insecticides and acaricides are:

| | |
|---|---|
| 1. | Abamectin |
| 2. | AC 303 630 |
| 3. | Acephat |
| 4. | Acrinathrin |
| 5. | Alanycarb |
| 6. | Aldicarb |
| 7. | α-Cypermethrin |
| 8. | Alphamethrin |
| 9. | Amitraz |
| 10. | Avermectin $B_1$ |
| 11. | AZ 60541 |
| 12. | Azinphos A |
| 13. | Azinphos M |
| 14. | Azinphos-methyl |
| 15. | Azocyclotin |
| 16. | *Bacillus* subtil. toxin |
| 17. | Bendiocarb |
| 18. | Benfuracarb |
| 19. | Bensultap |
| 20. | β-Cyfluthrin |
| 21. | Bifenthrin |
| 22. | BPMC |
| 23. | Brofenprox |
| 24. | Bromophos A |
| 25. | Bufencarb |
| 26. | Buprofezin |
| 27. | Butocarboxin |
| 28. | Butylpyridaben |
| 29. | Cadusafos |
| 30. | Carbaryl |
| 31. | Carbofuran |
| 32. | Carbophenthion |
| 33. | Cartap |
| 34. | Chloethocarb |
| 35. | Chlorethoxyfos |
| 36. | Chlorfenapyr |
| 37. | Chlorfluazuron |
| 38. | Chlormephos |
| 39. | Chlorpyrifos |
| 40. | Cis-Resmethrin |
| 41. | Clocythrin |
| 42. | Clofentezin |
| 43. | Cyanophos |
| 44. | Cycloprothrin |
| 45. | Cyfluthrin |
| 46. | Cyhexatin |
| 47. | D 2341 |
| 48. | Deltamethrin |
| 49. | Demeton M |
| 50. | Demeton S |
| 51. | Demeton-S-methyl |
| 52. | Dibutylaminothio |
| 53. | Dichlofenthion |
| 54. | Dicliphos |
| 55. | Diethion |
| 56. | Diflubenzuron |
| 57. | Dimethoat |
| 58. | Dimethylvinphos |
| 59. | Dioxathion |
| 60. | DPX-MP062 |
| 61. | Edifenphos |
| 62. | Emamectin |
| 63. | Endosulfan |
| 64. | Esfenvalerat |
| 65. | Ethiofencarb |
| 66. | Ethion |
| 67. | Ethofenprox |
| 68. | Ethoprophos |
| 69. | Etrimphos |
| 70. | Fenamiphos |
| 71. | Fenazaquin |
| 72. | Fenbutatinoxid |
| 73. | Fenitrothion |
| 74. | Fenobucarb |
| 75. | Fenothiocarb |
| 76. | Fenoxycarb |
| 77. | Fenpropathrin |
| 78. | Fenpyrad |
| 79. | Fenpyroximate |
| 80. | Fenthion |
| 81. | Fenvalerate |
| 82. | Fipronil |
| 83. | Fluazinam |
| 84. | Fluazuron |
| 85. | Flucycloxuron |
| 86. | Flucythrinat |
| 87. | Flufenoxuron |
| 88. | Flufenprox |
| 89. | Fonophos |
| 90. | Formothion |
| 91. | Fosthiazat |
| 92. | Fubfenprox |
| 93. | HCH |
| 94. | Heptenophos |
| 95. | Hexaflumuron |
| 96. | Hexythiazox |
| 97. | Hydroprene |
| 98. | Imidacloprid |
| 99. | insect-active fungi |
| 100. | insect-active nematodes |
| 101. | insect-active viruses |
| 102. | Iprobenfos |
| 103. | Isofenphos |
| 104. | Isoprocarb |
| 105. | Isoxathion |
| 106. | Ivermectin |
| 107. | λ-Cyhalothrin |
| 108. | Lufenuron |
| 109. | Malathion |
| 110. | Mecarbam |
| 111. | Mesulfenphos |
| 112. | Metaldehyd |
| 113. | Methamidophos |

| | |
|---|---|
| 114. | Methiocarb |
| 115. | Methomyl |
| 116. | Methoprene |
| 117. | Metolcarb |
| 118. | Mevinphos |
| 119. | Milbemectin |
| 120. | Moxidectin |
| 121. | Naled |
| 122. | NC 184 |
| 123. | NI-25, Acetamiprid |
| 124. | Nitenpyram |
| 125. | Omethoat |
| 126. | Oxamyl |
| 127. | Oxydemethon M |
| 128. | Oxydeprofos |
| 129. | Parathion |
| 130. | Parathion-methyl |
| 131. | Permethrin |
| 132. | Phenthoat |
| 133. | Phorat |
| 134. | Phosalone |
| 135. | Phosmet |
| 136. | Phoxim |
| 137. | Pirimicarb |
| 138. | Pirimiphos A |
| 139. | Pirimiphos M |
| 140. | Promecarb |
| 141. | Propaphos |
| 142. | Propoxur |
| 143. | Prothiofos |
| 144. | Prothoat |
| 145. | Pyrachlophos |
| 146. | Pyradaphenthion |
| 147. | Pyresmethrin |
| 148. | Pyrethrum |
| 149. | Pyridaben |
| 150. | Pyrimidifen |
| 151. | Pyriproxyfen |
| 152. | RH 5992 |
| 153. | RH-2485 |
| 154. | Salithion |
| 155. | Sebufos |
| 156. | Silafluofen |
| 157. | Spinosad |
| 158. | Sulfotep |
| 159. | Sulprofos |
| 160. | Tebufenozide |
| 161. | Tebufenpyrad |
| 162. | Tebupirimphos |
| 163. | Teflubenzuron |
| 164. | Tefluthrin |
| 165. | Temephos |
| 166. | Terbam |
| 167. | Terbufos |
| 168. | Tetrachlorvinphos |
| 169. | Thiafenox |
| 170. | Thiodicarb |
| 171. | Thiofanox |
| 172. | Thionazin |
| 173. | Thuringiensin |
| 174. | Tralomethrin |
| 175. | Triarthen |
| 176. | Triazamate |
| 177. | Triazophos |
| 178. | Triazuron |
| 179. | Trichlorfon |
| 180. | Triflumuron |
| 181. | Trimethacarb |
| 182. | Vamidothion |
| 183. | XMC (3,5,-Xylyl-methylcarbamate) |
| 184. | Xylylcarb |
| 185. | YI 5301/5302 |
| 186. | ζ-Cypermethrin |
| 187. | Zetamethrin |

Non-limitative examples of suitable anthelminthics are named in the following, a few representatives have insecticidal and acaricidal activity in addition to the anthelminthic activity, and are partly already in the above list.

(A1) Praziquantel=2–Cyclohexylcarbonyl-4-oxo-1,2,3,6,7,11b-hexahydro-4H-pyrazino[2,1-α]isoquinoline (A2) Closantel=3,5-diiodo-N-[5-chloro-2-methyl-4-(α-cyano-4-chlorobenzyl)phenyl]-salicylamide (A3) Triclabendazole=5-chloro-6-(2,3-dichlorophenoxy)-2-methylthio-1H-benzimidazole (A4) Levamisol=L-(–)-2,3,5,6-tetrahydro-6-phenylimidazo[2,1b]thiazole (A5) Mebendazole=(5-benzoyl-1H-benzimidazol-2-yl)carbaminic acid methylester (A6) Omphalotin=a macrocyclic fermentation product of the fungus *Omphalotus olearius* described in WO 97/20857

(A7) Abamectin=avermectin B1

(A8) Ivermectin=22,23-dihydroavermectin B1

(A9) Moxidectin=5-O-demethyl-28-deoxy-25-(1,3-dimethyl-1-butenyl)-6,28-epoxy-23-(methoxyimino)-milbemycin B (A10) Doramectin=25–Cyclohexyl-5-O-emethyl-25-de(1-methylpropyl)-avermectin A1a (A11) Milbemectin=mixture of milbemycin A3 and milbemycin A4

(A12) Milbemvcinoxim=5-oxime of milbemectin

Non-limitative examples of suitable repellents and detachers are:

(R1) DEET (N, N-diethyl-m-toluamide)

(R2) KBR 3023 N-butyl-2-oxycarbonyl-(2-hydroxy)-piperidine (R3) Cvmiazole=N,-2,3-dihydro-3-methyl-1,3-thiazol-2-ylidene-2,4-xylidene The said partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature. Therefore, the following listing is restricted to a few places where they may be found by way of example.

(I) 2-Methyl-2-(methylthio)propionaldehyde-O-methylcarbamoyloxime (Aldicarb), from The Pesticide Manual, 11$^{th}$ Ed. (1997), The British Crop Protection Council, London, page 26;

(II) S-(3,4-dihydro-4-oxobenzo[d]-[1,2,3]-triazin-3-ylmethyl)O,O-dimethyl-phosphoro-dithioate (Azinphos-methyl), from The Pesticide Manual, 11$^{th}$Ed. (1997), The British Crop Protection Council, London, page 67;

(III) Ethyl-N-[2,3-dihydro-2,2-dimethylbenzofuran-7-yloxycarbonyl-(methyl)aminothio]-N-isopropyl-β-alaninate (Benfuracarb), from The Pesticide Manual, 11$^{th}$Ed. (1997), The British Crop Protection Council, London, page 96;

(IV) 2-Methylbiphenyl-3-ylmethyl-(Z)-(1RS)-cis-3-(2-chloro-3,3,3-trifluoroprop-1-enyl)-2,2-dimethylcyclopropanecarboxylate (Bifenthrin), from The Pesticide Manual, 11$^{th}$Ed. (1997), The British Crop Protection Council, London, page 118;

(V) 2-tert-butylimino-3-isopropyl-5-phenyl-1,3,5-thiadiazian-4-one (Buprofezin), from The Pesticide Manual, 11$^{th}$Ed. (1997), The British Crop Protection Council, London, page 157;

(VI) 2,3-Dihydro-2,2-dimethylbenzofuran-7-yl-methylcarbamate (Carbofuran), from The Pesticide Manual, 11$^{th}$Ed. (1997), The British Crop Protection Council, London, page 186;

(VII) 2,3-Dihydro-2,2-dimethylbenzofuran-7-yl-(dibutylaminothio)methylcarbamate (Carbosulfan), from The Pesticide Manual, 11th Ed. (1997), The British Crop Protection Council, London, page 188;

(VIII) S,S'-(2-dimethylaminotrimethylene)-bis(thiocarbamate) (Cartap), from The Pesticide Manual, 11th Ed. (1997), The British Crop Protection Council, London, page 193;

(IX) 1-[3,5-Dichloro-4-(3-chloro-5-trifluoromethyl-2-pyridyloxy)phenyl]-3-(2,6-difluoro-benzoyl)-urea (Chlorfluazuron), from The Pesticide Manual, 11th Ed. (1997), The British Crop Protection Council, London, page 213;

(X) O,O-diethyl-O-3,5,6-trichloro-2-pyridyl-phosphorothioate (Chlorpyrifos), from The Pesticide Manual, 11th Ed. (1997), The British Crop Protection Council, London, page 235;

(XI) (RS)-α-cyano-4-fluoro-3-phenoxybenzyl-(1RS,3RS; 1RS,3RS)-3-(2,2-dichlorovinyl)-2,2-di-methylcyclopropanecarboxylate (Cyfluthrin), from The Pesticide Manual, 11th Ed. (1997), The British Crop Protection Council, London, page 293;

(XII) Mixture of (S)-α-cyano-3-phenoxybenzyl-(Z)-(1R, 3R)-3-(2-chloro-3,3,3-trifluoro-propenyl)-2,2-dimethyl-cyclopropanecarboxylate and (R)-α-cyano-3-phenoxybenzyl-(2)-(1R,3R)-3-(2-chloro-3,3,3-trifluoropropenyl)-2,2-dimethylcyclopropanecarboxylate (Lambda-Cyhalothrin), from The Pesticide Manual, 11th Ed. (1997), The British Crop Protection Council, London, page 300;

(XIII) Racemate consisting of (S)-α-cyano-3-phenoxybenzyl-(Z)-(1R,3R)-3-(2,2-dichlorovinyl)-2,2-dimethylcyclopropanecarboxylate and (R)-α-cyano-3-phenoxybenzyl-(1S,3S)-3-(2,2-dichlorovinyl)-2,2-dimethylcyclopropanecarboxylate (Alpha-cypermethrin), from The Pesticide Manual, 11th Ed. (1997), The British Crop Protection Council, London, page 308;

(XIV) a mixture of the stereoisomers of (S)-α-cyano-3-phenoxybenzyl (1RS,3RS,1RS,3RS)-3-(2,2-dichlorovinyl)-2,2-dimethylcyclopropanecarboxylate (zeta-Cypermethrin), from The Pesticide Manual, 11th Ed. (1997), The British Crop Protection Council, London, page 314;

(XV) (S)-α-cyano-3-phenoxybenzyl-(1R,3R)-3-(2,2-dibromovinyl)-2,2-dimethylcyclopropanecarboxylate (Deltamethrin), from The Pesticide Manual, 11th Ed. (1997), The British Crop Protection Council, London, page 344;

(XVI) (4-chlorophenyl)-3-(2,6-difluorobenzoyl)urea (Diflubenzuron), from The Pesticide Manual, 11th Ed. (1997), The British Crop Protection Council, London, page 395;

(XVII) (1,4,5,6,7,7-Hexachloro-8,9,10-trinorborn-5-en-2,3-ylenebismethylene)-sulphite (Endosulfan), from The Pesticide Manual, 11th Ed. (1997), The British Crop Protection Council, London, page 459;

(XVIII) α-ethylthio-o-tolyl-methylcarbamate (Ethiofencarb), from The Pesticide Manual, 11th Ed. (1997), The British Crop Protection Council, London, page 479;

(XIX) O,O-dimethyl-O-4-nitro-m-tolyl-phosphorothioate (Fenitrothion), from The Pesticide Manual, 11th Ed. (1997), The British Crop Protection Council, London, page 514;

(XX) 2-sec-butylphenyl-methylcarbamate (Fenobucarb), from The Pesticide Manual, 11th Ed. (1997), The British Crop Protection Council, London, page 516;

(XXI) (RS)-α-cyano-3-phenoxybenzyl-(RS)-2-(4-chlorophenyl)-3-methylbutyrate (Fenvalerate), from The Pesticide Manual, 11th Ed. (1997), The British Crop Protection Council, London, page 539;

(XXII) S-[formyl(methyl)carbamoylmethyl]-O,O-dimethyl-phosphorodithioate (Formothion), from The Pesticide Manual, 11th Ed. (1997), The British Crop Protection Council, London, page 625;

(XXIII) 4-Methylthio-3,5-xylyl-methylcarbamate (Methiocarb), from The Pesticide Manual, 11th Ed. (1997), The British Crop Protection Council, London, page 813;

(XXIV) 7-chlorobicyclo[3.2.0]hepta-2,6-dien-6-yl-dimethylphosphate (Heptenophos), from The Pesticide Manual, 11th Ed. (1997), The British Crop Protection Council, London, page 670;

(XXV) 1-(6-chloro-3-pyridylmethyl)-N-nitroimidazolidin-2-ylidenamine (Imidacloprid), from The Pesticide Manual, 11th Ed. (1997), The British Crop Protection Council, London, page 706;

(XXVI) 2-isopropylphenyl-methylcarbamate (Isoprocarb), from The Pesticide Manual, 11th Ed. (1997), The British Crop Protection Council, London, page 729;

(XXVII) O,S-dimethyl-phosphoramidothioate (Methamidophos), from The Pesticide Manual, 11th Ed. (1997), The British Crop Protection Council, London, page 808;

(XXVIII) S-Methyl-N-(methylcarbamoyloxy)thioacetimidate (Methomyl), from The Pesticide Manual, 11th Ed. (1997), The British Crop Protection Council, London, page 815;

(XXIX) Methyl-3-(dimethoxyphosphinoyloxy)but-2-enoate (Mevinphos), from The Pesticide Manual, 11th Ed. (1997), The British Crop Protection Council, London, page 844;

(XXX) O,O-diethyl-O-4-nitrophenyl-phosphorothioate (Parathion), from The Pesticide Manual, 11th Ed. (1997), The British Crop Protection Council, London, page 926;

(XXXI) O,O-dimethyl-O-4-nitrophenyl-phosphorothioate (Parathion-methyl), from The Pesticide Manual, 11th Ed. (1997), The British Crop Protection Council, London, page 928;

(XXXII) S-6-chloro-2,3-dihydro-2-oxo-1,3-benzoxazol-3-ylmethyl-O,O-diethyl-phosphordithioate (Phosalone), from The Pesticide Manual, 11th Ed. (1997), The British Crop Protection Council, London, page 963;

(XXXIII) 2-Dimethylamino-5,6-dimethylpyrimidin-4-yl-dimethylcarbamate (Pirimicarb), from The Pesticide Manual, 11th Ed. (1997), The British Crop Protection Council, London, page 985;

(XXXIV) 2-isopropoxyphenyl-methylcarbamate (Propoxur), from The Pesticide Manual, 11th Ed. (1997), The British Crop Protection Council, London, page 1036;

(XXXV) 1-(3,5-dichloro-2,4-difluorophenyl)-3-(2,6-difluorobenzoyl)urea (Teflubenzuron), from The Pesticide Manual, 11th Ed. (1997), The British Crop Protection Council, London, page 1158;

(XXXVI) S-tert-butylthiomethyl-O,O-dimethyl-phosphorodithioate (Terbufos), from The Pesticide Manual, 11th Ed. (1997), The British Crop Protection Council, London, page 1165;

(XXXVII) ethyl-(3-tert.-butyl-1-dimethylcarbamoyl-1H-1, 2,4-triazol-5-yl-thio)-acetate, (Triazamate), from The Pesticide Manual, 11th Ed. (1997), The British Crop Protection Council, London, page 1224;

(XXXVIII) Abamectin, from The Pesticide Manual, 11th Ed. (1997), The British Crop Protection Council, London, page 3;

(XXXIX) 2-sec-butylphenyl-methylcarbamate (Fenobucarb), from The Pesticide Manual, 11th Ed. (1997), The British Crop Protection Council, London, page 516;

(XL) N-tert.-butyl-N-(4-ethylbenzoyl)-3,5-dimethylbenzohydrazide (Tebufenozide), from The Pesticide Manual, 11th Ed. (1997), The British Crop Protection Council, London, page 1147;

(XLI) (±)-5-amino-1-(2,6-dichloro-α,α,α-trifluoro-p-tolyl)-4-trifluoromethyl-sulphinylpyrazol-3-carbonitrile (Fipronil), from The Pesticide Manual, 11<sup>th</sup>Ed. (1997), The British Crop Protection Council, London, page 545;

(XLII) (RS)-α-cyano-4-fluoro-3-phenoxybenzyl(1RS,3RS; 1RS,3RS)-3-(2,2-dichloro-vinyl)-2,2-dimethylcyclopropanecarboxylate (beta-Cyfluthrin), from The Pesticide Manual, 11<sup>th</sup>Ed. (1997), The British Crop Protection Council, London, page 295;

(XLIII) (4-ethoxyphenyl)-[3-(4-fluoro-3-phenoxyphenyl) propyl](dimethyl)silane (Silafluofen), from The Pesticide Manual, 11<sup>th</sup>Ed. (1997), The British Crop Protection Council, London, page 1105;

(XLIV) tert.-butyl (E)-α-(1,3-dimethyl-5-phenoxypyrazol-4-yl-methylenamino-oxy)-p-toluate (Fenpyroximate), from The Pesticide Manual, 11<sup>th</sup>Ed. (1997), The British Crop Protection Council, London, page 530;

(XLV) 2-tert.-butyl-5-(4-tert.-butylbenzylthio)-4-chloropyridazin-3(2H)-one (Pyridaben), from The Pesticide Manual, 11<sup>th</sup>Ed. (1997), The British Crop Protection Council, London, page 1161;

(XLVI) 4-[[4-(1,1-dimethylphenyl)phenyl]ethoxy]-quinazoline (Fenazaquin), from The Pesticide Manual, 11<sup>th</sup>Ed. (1997), The British Crop Protection Council, London, page 507;

(XLVII) 4-phenoxyphenyl-(RS)-2-(pyridyloxy)propyl-ether (Pyriproxyfen), from The Pesticide Manual, 11<sup>th</sup>Ed. (1997), The British Crop Protection Council, London, page 1073;

(XLVIII) 5-chloro-N-{2-[4-(2-ethoxyethyl)-2,3-dimethylphenoxy]ethyl}-6-ethylpyrimidine-4-amine (Pyrimidifen), from The Pesticide Manual, 11<sup>th</sup>Ed. (1997), The British Crop Protection Council, London, page 1070;

(XLIX) (E)-N-(6-chloro-3-pyridylmethyl)-N-ethyl-N-methyl-2-nitrovinylidenediamine (Nitenpyram), from The Pesticide Manual, 11<sup>th</sup>Ed. (1997), The British Crop Protection Council, London, page 880;

(L) (E)-N$^1$-[(6-chloro-3-pyridyl)methyl]-N$^2$–Cyano-N$^1$-methylacetamidine (NI-25, Acetamiprid), from The Pesticide Manual, 11<sup>th</sup>Ed. (1997), The British Crop Protection Council, London, page 9;

(LI) Avermectin B$_1$, from The Pesticide Manual, 11<sup>th</sup>Ed. (1997), The British Crop Protection Council, London, page 3;

(LII) an insect-active extract from a plant, especially (2R, 6aS,12aS)-1,2,6,6a,12,12a-hexhydro-2-isopropenyl-8,9-dimethoxy-chromeno[3,4-b]furo[2,3-h]chromen-6-one (Rotenone), from The Pesticide Manual, 11<sup>th</sup>Ed. (1997), The British Crop Protection Council, London, page 1097; and an extract from *Azadirachta indica*, especially azadirachtin, from The Pesticide Manual, 11<sup>th</sup>Ed. (1997), The British Crop Protection Council, London, page 59; and (LIII) a preparation which contains insect-active nematodes, preferably *Heterorhabditis bacteriophora* and *Heterorhabditis megidis*, from The Pesticide Manual, 11<sup>th</sup>Ed. (1997), The British Crop Protection Council, London, page 671; *Steinernema feltiae*, from The Pesticide Manual, 11<sup>th</sup>Ed. (1997), The British Crop Protection Council, London, page 1115 and *Steinemema scapterisci*, from The Pesticide Manual, 11<sup>th</sup>Ed. (1997), The British Crop Protection Council, London, page 1116;

(LIV) a preparation obtainable from *Bacillus subtilis*, from The Pesticide Manual, 11<sup>th</sup>Ed. (1997), The British Crop Protection Council, London, page 72; or from a strain of *Bacillus thuringiensis* with the exception of compounds isolated from GC91 or from NCTC11821; The Pesticide Manual, 11<sup>th</sup>Ed. (1997), The British Crop Protection Council, London, page 73;

(LV) a preparation which contains insect-active fungi, preferably *Verticillium lecanii*, from The Pesticide Manual, 11<sup>th</sup>Ed. (1997), The British Crop Protection Council, London, page 1266; *Beauveria brogniartii*, from The Pesticide Manual, 11<sup>th</sup>Ed. (1997), The British Crop Protection Council, London, page 85 and *Beauveria bassiana*, from The Pesticide Manual, 11<sup>th</sup>Ed. (1997), The British Crop Protection Council, London, page 83;

(LVI) a preparation which contains insect-active viruses, preferably *Neodipridon* Sertifer NPV, from The Pesticide Manual, 11<sup>th</sup>Ed. (1997), The British Crop Protection Council, London, page 1342; *Mamestra brassicae* NPV, from The Pesticide Manual, 11<sup>th</sup>Ed. (1997), The British Crop Protection Council, London, page 759 and *Cydia pomonella* granulosis virus, from The Pesticide Manual, 11<sup>th</sup>Ed. (1997), The British Crop Protection Council, London, page 291;

(CLXXXI) 7-chloro-2,3,4a,5-tetrahydro-2-[methoxycarbonyl(4-trifluoromethoxyphenyl)-carbamoyl]indol[1,2e]oxazoline-4a-carboxylate (DPX-MP062, Indoxycarb), from The Pesticide Manual, 11<sup>th</sup>Ed. (1997), The British Crop Protection Council, London, page 453;

(CLXXXII) N-tert.-butyl-N'-(3,5-dimethylbenzoyl)-3-methoxy-2-methylbenzohydrazide (RH-2485, Methoxyfenozide), from The Pesticide Manual, 11<sup>th</sup>Ed. (1997), The British Crop Protection Council, London, page 1094; and (CLXXXIII) (N'-[4-methoxy-biphenyl-3-yl]-hydrazinecarboxylic acid isopropylester (D 2341), from Brighton Crop Protection Conference, 1996, 487-493;

(R2) Book of Abstracts, 212th ACS National Meeting Orlando, Fla., Aug. 25-29 (1996), AGRO-020. Publisher: American Chemical Society, Washington, D.C. CONEN: 63BFAF.

As a consequence of the above details, a further essential aspect of the present invention relates to combination preparations for the control of parasites on warm-blooded animals, characterised in that they contain, in addition to a compound of formula I, at least one further active ingredient having the same or different sphere of activity and at least one physiologically acceptable carrier. The present invention is not restricted to two-fold combinations.

As a rule, the anthelminthic compositions according to the invention contain 0.1 to 99% by weight, especially 0.1 to 95% by weight of active ingredient of formula I, Ia or mixtures thereof, 99.9 to 1% by weight, especially 99.8 to 5% by weight of a solid or liquid admixture, including 0 to 25% by weight, especially 0.1 to 25% by weight of a surfactant.

Application of the compositions according to the invention to the animals to be treated may take place topically, perorally, parenterally or subcutaneously, the composition being present in the form of solutions, emulsions, suspensions, (drenches), powders, tablets, boli, capsules and pour-on formulations.

The pour-on or spot-on method consists in applying the compound of formula I to a specific location of the skin or coat, advantageously to the neck or backbone of the animal. This takes place e.g. by applying a swab or spray of the pour-on or spot-on formulation to a relatively small area of the coat, from where the active substance is dispersed almost automatically over wide areas of the fur owing to the spreading nature of the components in the formulation and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyidodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$–$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

A pour-on or spot-on formulation generally contains 1 to 20% by weight of a compound of formula I, 0.1 to 50% by weight of dispersing agent and 45 to 98.9% by weight of solvent.

The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

Whereas it is preferred to formulate commercial products as concentrates, the end user will normally use dilute formulations.

Such compositions may also contain further additives, such as stabilisers, anti-foaming agents, viscosity regulators, binding agents or tackifiers, as well as other active ingredients, in order to achieve special effects.

Anthelminthic compositions of this type, which are used by the end user, similarly form a constituent of the present invention.

In each of the processes according to the invention for pest control or in each of the pest control compositions according to the invention, the active ingredients of formula I can be used in all of their steric configurations or in mixtures thereof.

The invention also includes a method of prophylactically protecting warm-blooded animals, especially productive livestock, domestic animals and pets, against parasitic helminths, which is characterised in that the active ingredients of formula I or the active ingredient formulations prepared therefrom are administered to the animals as an additive to the feed, or to the drinks or also in solid or liquid form, orally or by injection or parenterally. The invention also includes the compounds of formula I according to the invention for usage in one of the said processes.

The following examples serve merely to illustrate the invention without restricting it, the term active ingredient representing a substance listed in tables.

In particular, preferred formulations are made up as follows:
(%=percent by weight)

FORMULATION EXAMPLES

| 1. Granulate | a) | b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent subsequently concentrated by evaporation under vacuum. Granulates of this kind can be mixed with the animal feed.

| 2. Granulate | |
|---|---|
| active ingredient | 3% |
| polyethylene glycol (mw 200) | 3% |
| kaolin | 94% |

(mw = molecular weight)

The finely ground active ingredient is evenly applied in a mixer to the kaolin which has been moistened with polyethylene glycol. In this way, dust-free coated granules are obtained.

| 3. Tablets or boli | | |
|---|---|---|
| I | active ingredient | 33.00% |
| | methylcellulose | 0.80% |
| | silicic acid, highly dispersed | 0.80% |
| | corn starch | 8.40% |
| II | lactose, cryst. | 22.50% |
| | corn starch | 17.00% |
| | microcryst. cellulose | 16.50% |
| | magnesium stearate | 1.00% |

I Methyl cellulose is stirred into water. After the material has swollen, silicic acid is stirred in and the mixture homogeneously suspended. The active ingredient and the corn starch are mixed. The aqueous suspension is worked into this mixture and kneaded to a dough. The resulting mass is granulated through a 12 M sieve and dried.

II All 4 excipients are mixed thoroughly.

III The preliminary mixes obtained according to I and II are mixed and pressed into tablets or boli.

| 4. Injectables A. Oily vehicle (slow release) | | |
|---|---|---|
| 1. | active ingredient | 0.1–1.0 g |
| | groundnut oil | ad 100 ml |
| 2. | active ingredient | 0.1–1.0 g |
| | sesame oil | ad 100 ml |

Preparation: The active ingredient is dissolved in part of the oil whilst stirring and, if required, with gentle heating, then after cooling made up to the desired volume and sterile-filtered through a suitable membrane filter with a pore size of 0.22 mm.

| B Water-miscible solvent (average rate of release) | |
| --- | --- |
| active ingredient | 0.1–1.0 g |
| 4-hydroxymethyl-1,3-dioxolane (glycerol formal) | 40 g |
| 1,2-propanediol | ad 100 ml |
| active ingredient | 0.1–1.0 g |
| glycerol dimethyl ketal | 40 g |
| 1,2-propanediol | ad 100 ml |

Preparation: The active ingredient is dissolved in part of the solvent whilst stirring, made up to the desired volume and sterile-filtered through a suitable membrane filter with a pore size of 0.22 mm.

| C. Aqueous solubilisate (rapid release) | | |
| --- | --- | --- |
| 1. | active ingredient | 0.1–1.0 g |
|    | polyethoxylated castor oil (40 ethylene oxide units) | 10 g |
|    | 1,2-propanediol | 20 g |
|    | benzyl alcohol | 1 g |
|    | aqua ad inject. | ad 100 ml |
| 2. | active ingredient | 0.1–1.0 g |
|    | polyethoxylated sorbitan monooleate (20 ethylene oxide units) | 8 g |
|    | 4-hydroxymethyl-1,3-dioxolane (glycerol formal) | 20 g |
|    | benzyl alcohol | 1 g |
|    | aqua ad inject. | ad 100 ml |

Preparation: The active ingredient is dissolved in the solvents and the surfactant, and made up with water to the desired volume. Sterile filtration through an appropriate membrane filter of 0.22 mm pore size.

| 5. Pour on | |
| --- | --- |
| A. | |
| active ingredient | 5 g |
| isopropyl myristate | 10 g |
| isopropanol | ad 100 ml |
| B | |
| active ingredient | 2 g |
| hexyl laurate | 5 g |
| medium-chained triglyceride | 15 g |
| ethanol | ad 100 ml |
| C. | |
| active ingredient | 2 g |
| oleyl oleate | 5 g |
| N-methyl-pyrrolidone | 40 g |
| isopropanol | ad 100 ml |

The aqueous systems may also preferably be used for oral and/or intraruminal application.

The compositions may also contain further additives, such as stabilisers, e.g. where appropriate epoxidised vegetable oils (epoxidised coconut oil, rapeseed oil, or soybean oil); antifoams, e.g. silicone oil, preservatives, viscosity regulators, binders, tackifiers, as well as fertilisers or other active ingredients to achieve special effects.

Further biologically active substances or additives, which are neutral towards the compounds of formula I and do not have a harmful effect on the host animal to be treated, as well as mineral salts or vitamins, may also be added to the described compositions.

The following examples serve to illustrate the invention. They do not limit the invention. The letter 'h' stands for hour. The starting substances used may be produced by methods described in literature or are commercially available.

PREPARATION EXAMPLES

Example 1

3-(2-chlorophenoxy)-2-hydroxy-2-methylpropionitrile 1.02 g of 1-(2-chlorophenoxy)-propan-2-one and 0.71 g of sodium cyanide are dissolved in

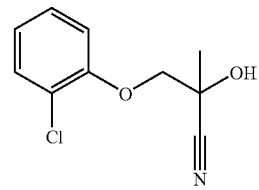

a mixture of 6 ml of $H_2O$ and 10 ml of diethylether. Subsequently, 1.2 ml of conc. hydrochloric acid are added dropwise at an internal temperature of 0-5° C. After stirring the reaction mixture for 3 hours at 0-5° C., the organic phase is separated and the aqueous phase is extracted twice with diethylether. The organic phases are combined, dried over sodium sulphate and the solvent removed. In this way, 1.10 g of the title compound are obtained as a colourless oil.

Example 2

4-trifluoromethoxybenzoic acid-2-(2-chlorphenoxy)-1–Cyano-1-methyl-ethyl ester 212 mg of 3-(2-chlorophenoxy)-2-hydroxy-2-methylpropionitrile and 270 mg of 4-trifluoromethoxybenzoic

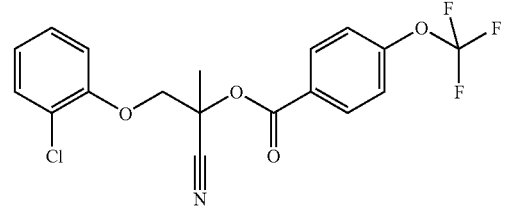

acid chloride are dissolved in 15 ml of $CH_2Cl_2$, and at an internal temperature of 0-5° C., 122 mg of triethylamine, dissolved in 5 ml of $CH_2Cl_2$, are added dropwise. After adding 25 mg of dimethylamino pyridine, the reaction mixture is stirred for 20 h at 0-5° C., subsequently washed with each of 1 N hydrochloric acid, saturated sodium bicarbonate solution and brine, and the organic phase is separated. The organic phase is dried over magnesium sulphate, the solvent removed and the residue chromatographed over silica gel ($CH_2Cl_2$/cyclohexane: 1:3). In this way, 220 mg of the title compound are obtained as a colourless oil.

Example 3

4-trifluoromethylphenyl)-carbamic acid-2-(2-chlorphenoxy)-1–Cyano-1-methyl-ethylester 254 mg of 3-(2-chlorophenoxy)-2-hydroxy-2-methylpropionitrile and 262 mg of 4-trifluoromethylphenyl

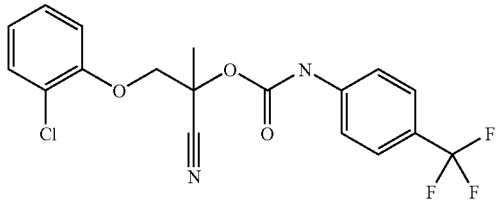

isocyanate are dissolved in 20 ml of $CH_2Cl_2$, and at room temperature, 142 mg of triethylamine, dissolved in 5 ml of $CH_2Cl_2$, are added dropwise. The reaction mixture is stirred for 7 h at room temperature, and subsequently washed with each of 1 N hydrochloric acid, saturated sodium bicarbonate solution and brine. The organic phase is dried over magnesium sulphate, the solvent removed and the residue chromatographed over silica gel (ethyl acetate/cyclohexane: 1:1). Following crystallisation from diethylether/hexane, 150 mg of the title compound are obtained as colourless crystals of m.p.: 142-3° C.

The substances named in the following table may also be prepared analogously to the above-described method.

TABLE 1

| No. | X | $R_1$ | $R_2$ | phys. data |
|---|---|---|---|---|
| 1.1 | — | H | H | |
| 1.2 | — | H | 2-$CH_3$ | |
| 1.3 | — | H | 3-$CH_3$ | |
| 1.4 | — | H | 4-$CH_3$ | |
| 1.5 | — | H | 2-F | |
| 1.6 | — | H | 3-F | |
| 1.7 | — | H | 4-F | |
| 1.8 | — | H | 2-Cl | |
| 1.9 | — | H | 3-Cl | |
| 1.10 | — | H | 4-Cl | |
| 1.11 | — | H | 2-$CF_3$ | |
| 1.12 | — | H | 3-$CF_3$ | |
| 1.13 | — | H | 4-$CF_3$ | |
| 1.14 | — | H | 2-$OCF_3$ | |
| 1.15 | — | H | 3-$OCF_3$ | |
| 1.16 | — | H | 4-$OCF_3$ | |
| 1.17 | — | H | 2,3-$Cl_2$ | |
| 1.18 | — | H | 2,4-$Cl_2$ | |
| 1.19 | — | H | 2,5-$Cl_2$ | |
| 1.20 | — | H | 2,6-$Cl_2$ | |
| 1.21 | — | H | 3,4-$Cl_2$ | |
| 1.22 | — | H | 3,5-$Cl_2$ | |
| 1.23 | — | 2-$CH_3$ | H | |
| 1.24 | — | 2-$CH_3$ | 2-$CH_3$ | |
| 1.25 | — | 2-$CH_3$ | 3-$CH_3$ | |
| 1.26 | — | 2-$CH_3$ | 4-$CH_3$ | |
| 1.27 | — | 2-$CH_3$ | 2-F | |
| 1.28 | — | 2-$CH_3$ | 3-F | |
| 1.29 | — | 2-$CH_3$ | 4-F | |
| 1.30 | — | 2-$CH_3$ | 2-Cl | |
| 1.31 | — | 2-$CH_3$ | 3-Cl | |
| 1.32 | — | 2-$CH_3$ | 4-Cl | |
| 1.33 | — | 2-$CH_3$ | 2-$CF_3$ | |
| 1.34 | — | 2-$CH_3$ | 3-$CF_3$ | |
| 1.35 | — | 2-$CH_3$ | 4-$CF_3$ | |
| 1.36 | — | 2-$CH_3$ | 2-$OCF_3$ | |
| 1.37 | — | 2-$CH_3$ | 3-$OCF_3$ | |
| 1.38 | — | 2-$CH_3$ | 4-$OCF_3$ | |
| 1.39 | — | 2-$CH_3$ | 2,3-$Cl_2$ | |
| 1.40 | — | 2-$CH_3$ | 2,4-$Cl_2$ | |
| 1.41 | — | 2-$CH_3$ | 2,5-$Cl_2$ | |
| 1.42 | — | 2-$CH_3$ | 2,6-$Cl_2$ | |
| 1.43 | — | 2-$CH_3$ | 3,4-$Cl_2$ | |
| 1.44 | — | 2-$CH_3$ | 3,5-$Cl_2$ | |
| 1.45 | — | 3-$CH_3$ | H | |
| 1.46 | — | 3-$CH_3$ | 2-$CH_3$ | |
| 1.47 | — | 3-$CH_3$ | 3-$CH_3$ | |
| 1.48 | — | 3-$CH_3$ | 4-$CH_3$ | |
| 1.49 | — | 3-$CH_3$ | 2-F | |
| 1.50 | — | 3-$CH_3$ | 3-F | |
| 1.51 | — | 3-$CH_3$ | 4-F | |
| 1.52 | — | 3-$CH_3$ | 2-Cl | |
| 1.53 | — | 3-$CH_3$ | 3-Cl | |
| 1.54 | — | 3-$CH_3$ | 4-Cl | |
| 1.55 | — | 3-$CH_3$ | 2-$CF_3$ | |
| 1.56 | — | 3-$CH_3$ | 3-$CF_3$ | |
| 1.57 | — | 3-$CH_3$ | 4-$CF_3$ | |
| 1.58 | — | 3-$CH_3$ | 2-$OCF_3$ | |
| 1.59 | — | 3-$CH_3$ | 3-$OCF_3$ | |
| 1.60 | — | 3-$CH_3$ | 4-$OCF_3$ | |
| 1.61 | — | 3-$CH_3$ | 2,3-$Cl_2$ | |
| 1.62 | — | 3-$CH_3$ | 2,4-$Cl_2$ | |
| 1.63 | — | 3-$CH_3$ | 2,5-$Cl_2$ | |
| 1.64 | — | 3-$CH_3$ | 2,6-$Cl_2$ | |
| 1.65 | — | 3-$CH_3$ | 3,4-$Cl_2$ | |
| 1.66 | — | 3-$CH_3$ | 3,5-$Cl_2$ | |
| 1.67 | — | 4-$CH_3$ | H | |
| 1.68 | — | 4-$CH_3$ | 2-$CH_3$ | |
| 1.69 | — | 4-$CH_3$ | 3-$CH_3$ | |
| 1.70 | — | 4-$CH_3$ | 4-$CH_3$ | |
| 1.71 | — | 4-$CH_3$ | 2-F | |
| 1.72 | — | 4-$CH_3$ | 3-F | |
| 1.73 | — | 4-$CH_3$ | 4-F | |
| 1.74 | — | 4-$CH_3$ | 2-Cl | |
| 1.75 | — | 4-$CH_3$ | 3-Cl | |
| 1.76 | — | 4-$CH_3$ | 4-Cl | |
| 1.77 | — | 4-$CH_3$ | 2-$CF_3$ | |
| 1.78 | — | 4-$CH_3$ | 3-$CF_3$ | |
| 1.79 | — | 4-$CH_3$ | 4-$CF_3$ | |
| 1.80 | — | 4-$CH_3$ | 2-$OCF_3$ | |
| 1.81 | — | 4-$CH_3$ | 3-$OCF_3$ | |
| 1.82 | — | 4-$CH_3$ | 4-$OCF_3$ | |
| 1.83 | — | 4-$CH_3$ | 2,3-$Cl_2$ | |
| 1.84 | — | 4-$CH_3$ | 2,4-$Cl_2$ | |
| 1.85 | — | 4-$CH_3$ | 2,5-$Cl_2$ | |
| 1.86 | — | 4-$CH_3$ | 2,6-$Cl_2$ | |
| 1.87 | — | 4-$CH_3$ | 3,4-$Cl_2$ | |
| 1.88 | — | 4-$CH_3$ | 3,5-$Cl_2$ | |
| 1.89 | — | 2-F | H | |
| 1.90 | — | 2-F | 2-$CH_3$ | |
| 1.91 | — | 2-F | 3-$CH_3$ | |
| 1.92 | — | 2-F | 4-$CH_3$ | |
| 1.93 | — | 2-F | 2-F | |
| 1.94 | — | 2-F | 3-F | |
| 1.95 | — | 2-F | 4-F | |
| 1.96 | — | 2-F | 2-Cl | |
| 1.97 | — | 2-F | 3-Cl | |

TABLE 1-continued

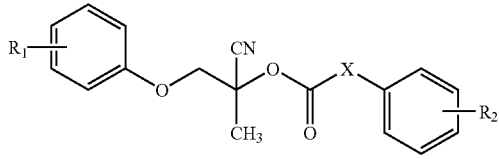

| No. | X | $R_1$ | $R_2$ | phys. data |
|---|---|---|---|---|
| 1.98 | — | 2-F | 4-Cl | |
| 1.99 | — | 2-F | 2-$CF_3$ | |
| 1.100 | — | 2-F | 3-$CF_3$ | |
| 1.101 | — | 2-F | 4-$CF_3$ | |
| 1.102 | — | 2-F | 2-$OCF_3$ | |
| 1.103 | — | 2-F | 3-$OCF_3$ | |
| 1.104 | — | 2-F | 4-$OCF_3$ | |
| 1.105 | — | 2-F | 2,3-$Cl_2$ | |
| 1.106 | — | 2-F | 2,4-$Cl_2$ | |
| 1.107 | — | 2-F | 2,5-$Cl_2$ | |
| 1.108 | — | 2-F | 2,6-$Cl_2$ | |
| 1.109 | — | 2-F | 3,4-$Cl_2$ | |
| 1.110 | — | 2-F | 3,5-$Cl_2$ | |
| 1.111 | — | 3-F | H | |
| 1.112 | — | 3-F | 2-$CH_3$ | |
| 1.113 | — | 3-F | 3-$CH_3$ | |
| 1.114 | — | 3-F | 4-$CH_3$ | |
| 1.115 | — | 3-F | 2-F | |
| 1.116 | — | 3-F | 3-F | |
| 1.117 | — | 3-F | 4-F | |
| 1.118 | — | 3-F | 2-Cl | |
| 1.119 | — | 3-F | 3-Cl | |
| 1.120 | — | 3-F | 4-Cl | |
| 1.121 | — | 3-F | 2-$CF_3$ | |
| 1.122 | — | 3-F | 3-$CF_3$ | |
| 1.123 | — | 3-F | 4-$CF_3$ | |
| 1.124 | — | 3-F | 2-$OCF_3$ | |
| 1.125 | — | 3-F | 3-$OCF_3$ | |
| 1.126 | — | 3-F | 4-$OCF_3$ | |
| 1.127 | — | 3-F | 2,3-$Cl_2$ | |
| 1.128 | — | 3-F | 2,4-$Cl_2$ | |
| 1.129 | — | 3-F | 2,5-$Cl_2$ | |
| 1.130 | — | 3-F | 2,6-$Cl_2$ | |
| 1.131 | — | 3-F | 3,4-$Cl_2$ | |
| 1.132 | — | 3-F | 3,5-$Cl_2$ | |
| 1.133 | — | 4-F | H | |
| 1.134 | — | 4-F | 2-$CH_3$ | |
| 1.135 | — | 4-F | 3-$CH_3$ | |
| 1.136 | — | 4-F | 4-$CH_3$ | |
| 1.137 | — | 4-F | 2-F | |
| 1.138 | — | 4-F | 3-F | |
| 1.139 | — | 4-F | 4-F | |
| 1.140 | — | 4-F | 2-Cl | |
| 1.141 | — | 4-F | 3-Cl | |
| 1.142 | — | 4-F | 4-Cl | |
| 1.143 | — | 4-F | 2-$CF_3$ | |
| 1.144 | — | 4-F | 3-$CF_3$ | |
| 1.145 | — | 4-F | 4-$CF_3$ | |
| 1.146 | — | 4-F | 2-$OCF_3$ | |
| 1.147 | — | 4-F | 3-$OCF_3$ | |
| 1.148 | — | 4-F | 4-$OCF_3$ | |
| 1.149 | — | 4-F | 2,3-$Cl_2$ | |
| 1.150 | — | 4-F | 2,4-$Cl_2$ | |
| 1.151 | — | 4-F | 2,5-$Cl_2$ | |
| 1.152 | — | 4-F | 2,6-$Cl_2$ | |
| 1.153 | — | 4-F | 3,4-$Cl_2$ | |
| 1.154 | — | 4-F | 3,5-$Cl_2$ | |
| 1.155 | — | 2-Cl | H | |
| 1.156 | — | 2-Cl | 2-$CH_3$ | |
| 1.157 | — | 2-Cl | 3-$CH_3$ | |
| 1.158 | — | 2-Cl | 4-$CH_3$ | |
| 1.159 | — | 2-Cl | 2-F | |
| 1.160 | — | 2-Cl | 3-F | |
| 1.161 | — | 2-Cl | 4-F | |
| 1.162 | — | 2-Cl | 2-Cl | |
| 1.163 | — | 2-Cl | 3-Cl | |
| 1.164 | — | 2-Cl | 4-Cl | |
| 1.165 | — | 2-Cl | 2-$CF_3$ | |

TABLE 1-continued

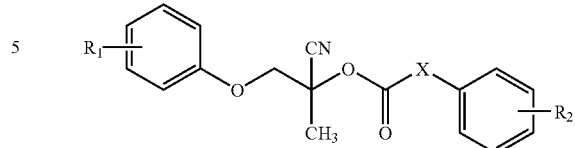

| No. | X | $R_1$ | $R_2$ | phys. data |
|---|---|---|---|---|
| 1.166 | — | 2-Cl | 3-$CF_3$ | |
| 1.167 | — | 2-Cl | 4-$CF_3$ | oil |
| 1.168 | — | 2-Cl | 2-$OCF_3$ | |
| 1.169 | — | 2-Cl | 3-$OCF_3$ | |
| 1.170 | — | 2-Cl | 4-$OCF_3$ | oil |
| 1.171 | — | 2-Cl | 2,3-$Cl_2$ | |
| 1.172 | — | 2-Cl | 2,4-$Cl_2$ | |
| 1.173 | — | 2-Cl | 2,5-$Cl_2$ | |
| 1.174 | — | 2-Cl | 2,6-$Cl_2$ | |
| 1.175 | — | 2-Cl | 3,4-$Cl_2$ | |
| 1.176 | — | 2-Cl | 3,5-$Cl_2$ | |
| 1.177 | — | 3-Cl | H | |
| 1.178 | — | 3-Cl | 2-$CH_3$ | |
| 1.179 | — | 3-Cl | 3-$CH_3$ | |
| 1.180 | — | 3-Cl | 4-$CH_3$ | |
| 1.181 | — | 3-Cl | 2-F | |
| 1.182 | — | 3-Cl | 3-F | |
| 1.183 | — | 3-Cl | 4-F | |
| 1.184 | — | 3-Cl | 2-Cl | |
| 1.185 | — | 3-Cl | 3-Cl | |
| 1.186 | — | 3-Cl | 4-Cl | |
| 1.187 | — | 3-Cl | 2-$CF_3$ | |
| 1.188 | — | 3-Cl | 3-$CF_3$ | |
| 1.189 | — | 3-Cl | 4-$CF_3$ | |
| 1.190 | — | 3-Cl | 2-$OCF_3$ | |
| 1.191 | — | 3-Cl | 3-$OCF_3$ | |
| 1.192 | — | 3-Cl | 4-$OCF_3$ | |
| 1.193 | — | 3-Cl | 2,3-$Cl_2$ | |
| 1.194 | — | 3-Cl | 2,4-$Cl_2$ | |
| 1.195 | — | 3-Cl | 2,5-$Cl_2$ | |
| 1.196 | — | 3-Cl | 2,6-$Cl_2$ | |
| 1.197 | — | 3-Cl | 3,4-$Cl_2$ | |
| 1.198 | — | 3-Cl | 3,5-$Cl_2$ | |
| 1.199 | — | 4-Cl | H | |
| 1.200 | — | 4-Cl | 2-$CH_3$ | |
| 1.201 | — | 4-Cl | 3-$CH_3$ | |
| 1.202 | — | 4-Cl | 4-$CH_3$ | |
| 1.203 | — | 4-Cl | 2-F | |
| 1.204 | — | 4-Cl | 3-F | |
| 1.205 | — | 4-Cl | 4-F | |
| 1.206 | — | 4-Cl | 2-Cl | |
| 1.207 | — | 4-Cl | 3-Cl | |
| 1.208 | — | 4-Cl | 4-Cl | |
| 1.209 | — | 4-Cl | 2-$CF_3$ | |
| 1.210 | — | 4-Cl | 3-$CF_3$ | |
| 1.211 | — | 4-Cl | 4-$CF_3$ | |
| 1.212 | — | 4-Cl | 2-$OCF_3$ | |
| 1.213 | — | 4-Cl | 3-$OCF_3$ | |
| 1.214 | — | 4-Cl | 4-$OCF_3$ | |
| 1.215 | — | 4-Cl | 2,3-$Cl_2$ | |
| 1.216 | — | 4-Cl | 2,4-$Cl_2$ | |
| 1.217 | — | 4-Cl | 2,5-$Cl_2$ | |
| 1.218 | — | 4-Cl | 2,6-$Cl_2$ | |
| 1.219 | — | 4-Cl | 3,4-$Cl_2$ | |
| 1.220 | — | 4-Cl | 3,5-$Cl_2$ | |
| 1.221 | — | 2-$CF_3$ | H | |
| 1.222 | — | 2-$CF_3$ | 2-$CH_3$ | |
| 1.223 | — | 2-$CF_3$ | 3-$CH_3$ | |
| 1.224 | — | 2-$CF_3$ | 4-$CH_3$ | |
| 1.225 | — | 2-$CF_3$ | 2-F | |
| 1.226 | — | 2-$CF_3$ | 3-F | |
| 1.227 | — | 2-$CF_3$ | 4-F | |
| 1.228 | — | 2-$CF_3$ | 2-Cl | |
| 1.229 | — | 2-$CF_3$ | 3-Cl | |
| 1.230 | — | 2-$CF_3$ | 4-Cl | |
| 1.231 | — | 2-$CF_3$ | 2-$CF_3$ | |
| 1.232 | — | 2-$CF_3$ | 3-$CF_3$ | |
| 1.233 | — | 2-$CF_3$ | 4-$CF_3$ | oil |

TABLE 1-continued

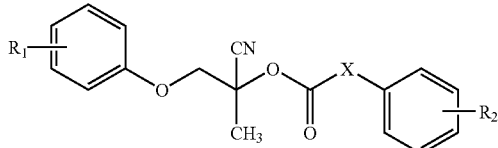

| No. | X | R₁ | R₂ | phys. data |
|---|---|---|---|---|
| 1.234 | — | 2-CF₃ | 2-OCF₃ | |
| 1.235 | — | 2-CF₃ | 3-OCF₃ | |
| 1.236 | — | 2-CF₃ | 4-OCF₃ | m.p. 66–8° |
| 1.237 | — | 2-CF₃ | 2,3-Cl₂ | |
| 1.238 | — | 2-CF₃ | 2,4-Cl₂ | |
| 1.239 | — | 2-CF₃ | 2,5-Cl₂ | |
| 1.240 | — | 2-CF₃ | 2,6-Cl₂ | |
| 1.241 | — | 2-CF₃ | 3,4-Cl₂ | |
| 1.242 | — | 2-CF₃ | 3,5-Cl₂ | |
| 1.243 | — | 3-CF₃ | H | |
| 1.244 | — | 3-CF₃ | 2-CH₃ | |
| 1.245 | — | 3-CF₃ | 3-CH₃ | |
| 1.246 | — | 3-CF₃ | 4-CH₃ | |
| 1.247 | — | 3-CF₃ | 2-F | |
| 1.248 | — | 3-CF₃ | 3-F | |
| 1.249 | — | 3-CF₃ | 4-F | |
| 1.250 | — | 3-CF₃ | 2-Cl | |
| 1.251 | — | 3-CF₃ | 3-Cl | |
| 1.252 | — | 3-CF₃ | 4-Cl | |
| 1.253 | — | 3-CF₃ | 2-CF₃ | |
| 1.254 | — | 3-CF₃ | 3-CF₃ | |
| 1.255 | — | 3-CF₃ | 4-CF₃ | |
| 1.256 | — | 3-CF₃ | 2-OCF₃ | |
| 1.257 | — | 3-CF₃ | 3-OCF₃ | |
| 1.258 | — | 3-CF₃ | 4-OCF₃ | |
| 1.259 | — | 3-CF₃ | 2,3-Cl₂ | |
| 1.260 | — | 3-CF₃ | 2,4-Cl₂ | |
| 1.261 | — | 3-CF₃ | 2,5-Cl₂ | |
| 1.262 | — | 3-CF₃ | 2,6-Cl₂ | |
| 1.263 | — | 3-CF₃ | 3,4-Cl₂ | |
| 1.264 | — | 3-CF₃ | 3,5-Cl₂ | |
| 1.265 | — | 4-CF₃ | H | |
| 1.266 | — | 4-CF₃ | 2-CH₃ | |
| 1.267 | — | 4-CF₃ | 3-CH₃ | |
| 1.268 | — | 4-CF₃ | 4-CH₃ | |
| 1.269 | — | 4-CF₃ | 2-F | |
| 1.270 | — | 4-CF₃ | 3-F | |
| 1.271 | — | 4-CF₃ | 4-F | |
| 1.272 | — | 4-CF₃ | 2-Cl | |
| 1.273 | — | 4-CF₃ | 3-Cl | |
| 1.274 | — | 4-CF₃ | 4-Cl | |
| 1.275 | — | 4-CF₃ | 2-CF₃ | |
| 1.276 | — | 4-CF₃ | 3-CF₃ | |
| 1.277 | — | 4-CF₃ | 4-CF₃ | |
| 1.278 | — | 4-CF₃ | 2-OCF₃ | |
| 1.279 | — | 4-CF₃ | 3-OCF₃ | |
| 1.280 | — | 4-CF₃ | 4-OCF₃ | |
| 1.281 | — | 4-CF₃ | 2,3-Cl₂ | |
| 1.282 | — | 4-CF₃ | 2,4-Cl₂ | |
| 1.283 | — | 4-CF₃ | 2,5-Cl₂ | |
| 1.284 | — | 4-CF₃ | 2,6-Cl₂ | |
| 1.285 | — | 4-CF₃ | 3,4-Cl₂ | |
| 1.286 | — | 4-CF₃ | 3,5-Cl₂ | |
| 1.287 | — | 2-OCF₃ | H | |
| 1.288 | — | 2-OCF₃ | 2-CH₃ | |
| 1.289 | — | 2-OCF₃ | 3-CH₃ | |
| 1.290 | — | 2-OCF₃ | 4-CH₃ | |
| 1.291 | — | 2-OCF₃ | 2-F | |
| 1.292 | — | 2-OCF₃ | 3-F | |
| 1.293 | — | 2-OCF₃ | 4-F | |
| 1.294 | — | 2-OCF₃ | 2-Cl | |
| 1.295 | — | 2-OCF₃ | 3-Cl | |
| 1.296 | — | 2-OCF₃ | 4-Cl | |
| 1.297 | — | 2-OCF₃ | 2-CF₃ | |
| 1.298 | — | 2-OCF₃ | 3-CF₃ | |
| 1.299 | — | 2-OCF₃ | 4-CF₃ | |
| 1.300 | — | 2-OCF₃ | 2-OCF₃ | |
| 1.301 | — | 2-OCF₃ | 3-OCF₃ | |

TABLE 1-continued

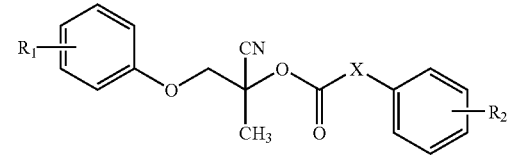

| No. | X | R₁ | R₂ | phys. data |
|---|---|---|---|---|
| 1.302 | — | 2-OCF₃ | 4-OCF₃ | |
| 1.303 | — | 2-OCF₃ | 2,3-Cl₂ | |
| 1.304 | — | 2-OCF₃ | 2,4-Cl₂ | |
| 1.305 | — | 2-OCF₃ | 2,5-Cl₂ | |
| 1.306 | — | 2-OCF₃ | 2,6-Cl₂ | |
| 1.307 | — | 2-OCF₃ | 3,4-Cl₂ | |
| 1.308 | — | 2-OCF₃ | 3,5-Cl₂ | |
| 1.309 | — | 3-OCF₃ | H | |
| 1.310 | — | 3-OCF₃ | 2-CH₃ | |
| 1.311 | — | 3-OCF₃ | 3-CH₃ | |
| 1.312 | — | 3-OCF₃ | 4-CH₃ | |
| 1.313 | — | 3-OCF₃ | 2-F | |
| 1.314 | — | 3-OCF₃ | 3-F | |
| 1.315 | — | 3-OCF₃ | 4-F | |
| 1.316 | — | 3-OCF₃ | 2-Cl | |
| 1.317 | — | 3-OCF₃ | 3-Cl | |
| 1.318 | — | 3-OCF₃ | 4-Cl | |
| 1.319 | — | 3-OCF₃ | 2-CF₃ | |
| 1.320 | — | 3-OCF₃ | 3-CF₃ | |
| 1.321 | — | 3-OCF₃ | 4-CF₃ | |
| 1.322 | — | 3-OCF₃ | 2-OCF₃ | |
| 1.323 | — | 3-OCF₃ | 3-OCF₃ | |
| 1.324 | — | 3-OCF₃ | 4-OCF₃ | |
| 1.325 | — | 3-OCF₃ | 2,3-Cl₂ | |
| 1.326 | — | 3-OCF₃ | 2,4-Cl₂ | |
| 1.327 | — | 3-OCF₃ | 2,5-Cl₂ | |
| 1.328 | — | 3-OCF₃ | 2,6-Cl₂ | |
| 1.329 | — | 3-OCF₃ | 3,4-Cl₂ | |
| 1.330 | — | 3-OCF₃ | 3,5-Cl₂ | |
| 1.331 | — | 4-OCF₃ | H | |
| 1.332 | — | 4-OCF₃ | 2-CH₃ | |
| 1.333 | — | 4-OCF₃ | 3-CH₃ | |
| 1.334 | — | 4-OCF₃ | 4-CH₃ | |
| 1.335 | — | 4-OCF₃ | 2-F | |
| 1.336 | — | 4-OCF₃ | 3-F | |
| 1.337 | — | 4-OCF₃ | 4-F | |
| 1.338 | — | 4-OCF₃ | 2-Cl | |
| 1.339 | — | 4-OCF₃ | 3-Cl | |
| 1.340 | — | 4-OCF₃ | 4-Cl | |
| 1.341 | — | 4-OCF₃ | 2-CF₃ | |
| 1.342 | — | 4-OCF₃ | 3-CF₃ | |
| 1.343 | — | 4-OCF₃ | 4-CF₃ | |
| 1.344 | — | 4-OCF₃ | 2-OCF₃ | |
| 1.345 | — | 4-OCF₃ | 3-OCF₃ | |
| 1.346 | — | 4-OCF₃ | 4-OCF₃ | |
| 1.347 | — | 4-OCF₃ | 2,3-Cl₂ | |
| 1.348 | — | 4-OCF₃ | 2,4-Cl₂ | |
| 1.349 | — | 4-OCF₃ | 2,5-Cl₂ | |
| 1.350 | — | 4-OCF₃ | 2,6-Cl₂ | |
| 1.351 | — | 4-OCF₃ | 3,4-Cl₂ | |
| 1.352 | — | 4-OCF₃ | 3,5-Cl₂ | |
| 1.353 | — | 2,3-Cl₂ | H | |
| 1.354 | — | 2,3-Cl₂ | 2-CH₃ | |
| 1.355 | — | 2,3-Cl₂ | 3-CH₃ | |
| 1.356 | — | 2,3-Cl₂ | 4-CH₃ | |
| 1.357 | — | 2,3-Cl₂ | 2-F | |
| 1.358 | — | 2,3-Cl₂ | 3-F | |
| 1.359 | — | 2,3-Cl₂ | 4-F | |
| 1.360 | — | 2,3-Cl₂ | 2-Cl | |
| 1.361 | — | 2,3-Cl₂ | 3-Cl | |
| 1.362 | — | 2,3-Cl₂ | 4-Cl | |
| 1.363 | — | 2,3-Cl₂ | 2-CF₃ | |
| 1.364 | — | 2,3-Cl₂ | 3-CF₃ | |
| 1.365 | — | 2,3-Cl₂ | 4-CF₃ | |
| 1.366 | — | 2,3-Cl₂ | 2-OCF₃ | |
| 1.367 | — | 2,3-Cl₂ | 3-OCF₃ | |
| 1.368 | — | 2,3-Cl₂ | 4-OCF₃ | |
| 1.369 | — | 2,3-Cl₂ | 2,3-Cl₂ | |

TABLE 1-continued

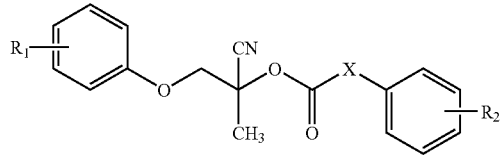

| No. | X | R₁ | R₂ | phys. data |
|---|---|---|---|---|
| 1.370 | — | 2,3-Cl₂ | 2,4-Cl₂ | |
| 1.371 | — | 2,3-Cl₂ | 2,5-Cl₂ | |
| 1.372 | — | 2,3-Cl₂ | 2,6-Cl₂ | |
| 1.373 | — | 2,3-Cl₂ | 3,4-Cl₂ | |
| 1.374 | — | 2,3-Cl₂ | 3,5-Cl₂ | |
| 1.375 | — | 2,4-Cl₂ | H | |
| 1.376 | — | 2,4-Cl₂ | 2-CH₃ | |
| 1.377 | — | 2,4-Cl₂ | 3-CH₃ | |
| 1.378 | — | 2,4-Cl₂ | 4-CH₃ | |
| 1.379 | — | 2,4-Cl₂ | 2-F | |
| 1.380 | — | 2,4-Cl₂ | 3-F | |
| 1.381 | — | 2,4-Cl₂ | 4-F | |
| 1.382 | — | 2,4-Cl₂ | 2-Cl | |
| 1.383 | — | 2,4-Cl₂ | 3-Cl | |
| 1.384 | — | 2,4-Cl₂ | 4-Cl | |
| 1.385 | — | 2,4-Cl₂ | 2-CF₃ | |
| 1.386 | — | 2,4-Cl₂ | 3-CF₃ | |
| 1.387 | — | 2,4-Cl₂ | 4-CF₃ | |
| 1.388 | — | 2,4-Cl₂ | 2-OCF₃ | |
| 1.389 | — | 2,4-Cl₂ | 3-OCF₃ | |
| 1.390 | — | 2,4-Cl₂ | 4-OCF₃ | |
| 1.391 | — | 2,4-Cl₂ | 2,3-Cl₂ | |
| 1.392 | — | 2,4-Cl₂ | 2,4-Cl₂ | |
| 1.393 | — | 2,4-Cl₂ | 2,5-Cl₂ | |
| 1.394 | — | 2,4-Cl₂ | 2,6-Cl₂ | |
| 1.395 | — | 2,4-Cl₂ | 3,4-Cl₂ | |
| 1.396 | — | 2,4-Cl₂ | 3,5-Cl₂ | |
| 1.397 | — | 2,5-Cl₂ | H | |
| 1.398 | — | 2,5-Cl₂ | 2-CH₃ | |
| 1.399 | — | 2,5-Cl₂ | 3-CH₃ | |
| 1.400 | — | 2,5-Cl₂ | 4-CH₃ | |
| 1.401 | — | 2,5-Cl₂ | 2-F | |
| 1.402 | — | 2,5-Cl₂ | 3-F | |
| 1.403 | — | 2,5-Cl₂ | 4-F | |
| 1.404 | — | 2,5-Cl₂ | 2-Cl | |
| 1.405 | — | 2,5-Cl₂ | 3-Cl | |
| 1.406 | — | 2,5-Cl₂ | 4-Cl | |
| 1.407 | — | 2,5-Cl₂ | 2-CF₃ | |
| 1.408 | — | 2,5-Cl₂ | 3-CF₃ | |
| 1.409 | — | 2,5-Cl₂ | 4-CF₃ | |
| 1.410 | — | 2,5-Cl₂ | 2-OCF₃ | |
| 1.411 | — | 2,5-Cl₂ | 3-OCF₃ | |
| 1.412 | — | 2,5-Cl₂ | 4-OCF₃ | |
| 1.413 | — | 2,5-Cl₂ | 2,3-Cl₂ | |
| 1.414 | — | 2,5-Cl₂ | 2,4-Cl₂ | |
| 1.415 | — | 2,5-Cl₂ | 2,5-Cl₂ | |
| 1.416 | — | 2,5-Cl₂ | 2,6-Cl₂ | |
| 1.417 | — | 2,5-Cl₂ | 3,4-Cl₂ | |
| 1.418 | — | 2,5-Cl₂ | 3,5-Cl₂ | |
| 1.419 | — | 2,6-Cl₂ | H | |
| 1.420 | — | 2,6-Cl₂ | 2-CH₃ | |
| 1.421 | — | 2,6-Cl₂ | 3-CH₃ | |
| 1.422 | — | 2,6-Cl₂ | 4-CH₃ | |
| 1.423 | — | 2,6-Cl₂ | 2-F | |
| 1.424 | — | 2,6-Cl₂ | 3-F | |
| 1.425 | — | 2,6-Cl₂ | 4-F | |
| 1.426 | — | 2,6-Cl₂ | 2-Cl | |
| 1.427 | — | 2,6-Cl₂ | 3-Cl | |
| 1.428 | — | 2,6-Cl₂ | 4-Cl | |
| 1.429 | — | 2,6-Cl₂ | 2-CF₃ | |
| 1.430 | — | 2,6-Cl₂ | 3-CF₃ | |
| 1.431 | — | 2,6-Cl₂ | 4-CF₃ | |
| 1.432 | — | 2,6-Cl₂ | 2-OCF₃ | |
| 1.433 | — | 2,6-Cl₂ | 3-OCF₃ | |
| 1.434 | — | 2,6-Cl₂ | 4-OCF₃ | |
| 1.435 | — | 2,6-Cl₂ | 2,3-Cl₂ | |
| 1.436 | — | 2,6-Cl₂ | 2,4-Cl₂ | |
| 1.437 | — | 2,6-Cl₂ | 2,5-Cl₂ | |

TABLE 1-continued

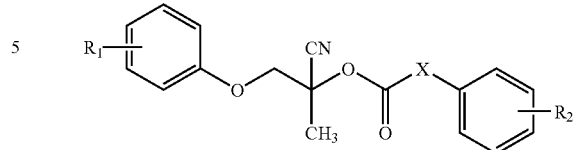

| No. | X | R₁ | R₂ | phys. data |
|---|---|---|---|---|
| 1.438 | — | 2,6-Cl₂ | 2,6-Cl₂ | |
| 1.439 | — | 2,6-Cl₂ | 3,4-Cl₂ | |
| 1.440 | — | 2,6-Cl₂ | 3,5-Cl₂ | |
| 1.441 | — | 3,4-Cl₂ | H | |
| 1.442 | — | 3,4-Cl₂ | 2-CH₃ | |
| 1.443 | — | 3,4-Cl₂ | 3-CH₃ | |
| 1.444 | — | 3,4-Cl₂ | 4-CH₃ | |
| 1.445 | — | 3,4-Cl₂ | 2-F | |
| 1.446 | — | 3,4-Cl₂ | 3-F | |
| 1.447 | — | 3,4-Cl₂ | 4-F | |
| 1.448 | — | 3,4-Cl₂ | 2-Cl | |
| 1.449 | — | 3,4-Cl₂ | 3-Cl | |
| 1.450 | — | 3,4-Cl₂ | 4-Cl | |
| 1.451 | — | 3,4-Cl₂ | 2-CF₃ | |
| 1.452 | — | 3,4-Cl₂ | 3-CF₃ | |
| 1.453 | — | 3,4-Cl₂ | 4-CF₃ | |
| 1.454 | — | 3,4-Cl₂ | 2-OCF₃ | |
| 1.455 | — | 3,4-Cl₂ | 3-OCF₃ | |
| 1.456 | — | 3,4-Cl₂ | 4-OCF₃ | |
| 1.457 | — | 3,4-Cl₂ | 2,3-Cl₂ | |
| 1.458 | — | 3,4-Cl₂ | 2,4-Cl₂ | |
| 1.459 | — | 3,4-Cl₂ | 2,5-Cl₂ | |
| 1.460 | — | 3,4-Cl₂ | 2,6-Cl₂ | |
| 1.461 | — | 3,4-Cl₂ | 3,4-Cl₂ | |
| 1.462 | — | 3,4-Cl₂ | 3,5-Cl₂ | |
| 1.463 | — | 3,5-Cl₂ | H | |
| 1.464 | — | 3,5-Cl₂ | 2-CH₃ | |
| 1.465 | — | 3,5-Cl₂ | 3-CH₃ | |
| 1.466 | — | 3,5-Cl₂ | 4-CH₃ | |
| 1.467 | — | 3,5-Cl₂ | 2-F | |
| 1.468 | — | 3,5-Cl₂ | 3-F | |
| 1.469 | — | 3,5-Cl₂ | 4-F | |
| 1.470 | — | 3,5-Cl₂ | 2-Cl | |
| 1.471 | — | 3,5-Cl₂ | 3-Cl | |
| 1.472 | — | 3,5-Cl₂ | 4-Cl | |
| 1.473 | — | 3,5-Cl₂ | 2-CF₃ | |
| 1.474 | — | 3,5-Cl₂ | 3-CF₃ | |
| 1.475 | — | 3,5-Cl₂ | 4-CF₃ | |
| 1.476 | — | 3,5-Cl₂ | 2-OCF₃ | |
| 1.477 | — | 3,5-Cl₂ | 3-OCF₃ | |
| 1.478 | — | 3,5-Cl₂ | 4-OCF₃ | |
| 1.479 | — | 3,5-Cl₂ | 2,3-Cl₂ | |
| 1.480 | — | 3,5-Cl₂ | 2,4-Cl₂ | |
| 1.481 | — | 3,5-Cl₂ | 2,5-Cl₂ | |
| 1.482 | — | 3,5-Cl₂ | 2,6-Cl₂ | |
| 1.483 | — | 3,5-Cl₂ | 3,4-Cl₂ | |
| 1.484 | — | 3,5-Cl₂ | 3,5-Cl₂ | |
| 1.485 | NH | H | H | |
| 1.486 | NH | H | 2-CH₃ | |
| 1.487 | NH | H | 3-CH₃ | |
| 1.488 | NH | H | 4-CH₃ | |
| 1.489 | NH | H | 2-F | |
| 1.490 | NH | H | 3-F | |
| 1.491 | NH | H | 4-F | |
| 1.492 | NH | H | 2-Cl | |
| 1.493 | NH | H | 3-Cl | |
| 1.494 | NH | H | 4-Cl | |
| 1.495 | NH | H | 2-CF₃ | |
| 1.496 | NH | H | 3-CF₃ | |
| 1.497 | NH | H | 4-CF₃ | |
| 1.498 | NH | H | 2-OCF₃ | |
| 1.499 | NH | H | 3-OCF₃ | |
| 1.500 | NH | H | 4-OCF₃ | |
| 1.501 | NH | H | 2,3-Cl₂ | |
| 1.502 | NH | H | 2,4-Cl₂ | |
| 1.503 | NH | H | 2,5-Cl₂ | |
| 1.504 | NH | H | 2,6-Cl₂ | |
| 1.505 | NH | H | 3,4-Cl₂ | |

TABLE 1-continued

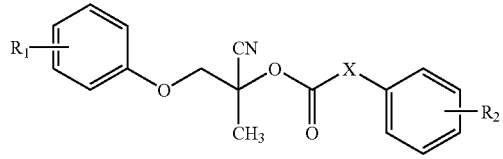

| No. | X | R₁ | R₂ | phys. data |
|---|---|---|---|---|
| 1.506 | NH | H | 3,5-Cl₂ | |
| 1.507 | NH | 2-CH₃ | H | |
| 1.508 | NH | 2-CH₃ | 2-CH₃ | |
| 1.509 | NH | 2-CH₃ | 3-CH₃ | |
| 1.510 | NH | 2-CH₃ | 4-CH₃ | |
| 1.511 | NH | 2-CH₃ | 2-F | |
| 1.512 | NH | 2-CH₃ | 3-F | |
| 1.513 | NH | 2-CH₃ | 4-F | |
| 1.514 | NH | 2-CH₃ | 2-Cl | |
| 1.515 | NH | 2-CH₃ | 3-Cl | |
| 1.516 | NH | 2-CH₃ | 4-Cl | |
| 1.517 | NH | 2-CH₃ | 2-CF₃ | |
| 1.518 | NH | 2-CH₃ | 3-CF₃ | |
| 1.519 | NH | 2-CH₃ | 4-CF₃ | |
| 1.520 | NH | 2-CH₃ | 2-OCF₃ | |
| 1.521 | NH | 2-CH₃ | 3-OCF₃ | |
| 1.522 | NH | 2-CH₃ | 4-OCF₃ | |
| 1.523 | NH | 2-CH₃ | 2,3-Cl₂ | |
| 1.524 | NH | 2-CH₃ | 2,4-Cl₂ | |
| 1.525 | NH | 2-CH₃ | 2,5-Cl₂ | |
| 1.526 | NH | 2-CH₃ | 2,6-Cl₂ | |
| 1.527 | NH | 2-CH₃ | 3,4-Cl₂ | |
| 1.528 | NH | 2-CH₃ | 3,5-Cl₂ | |
| 1.529 | NH | 3-CH₃ | H | |
| 1.530 | NH | 3-CH₃ | 2-CH₃ | |
| 1.531 | NH | 3-CH₃ | 3-CH₃ | |
| 1.532 | NH | 3-CH₃ | 4-CH₃ | |
| 1.533 | NH | 3-CH₃ | 2-F | |
| 1.534 | NH | 3-CH₃ | 3-F | |
| 1.535 | NH | 3-CH₃ | 4-F | |
| 1.536 | NH | 3-CH₃ | 2-Cl | |
| 1.537 | NH | 3-CH₃ | 3-Cl | |
| 1.538 | NH | 3-CH₃ | 4-Cl | |
| 1.539 | NH | 3-CH₃ | 2-CF₃ | |
| 1.540 | NH | 3-CH₃ | 3-CF₃ | |
| 1.541 | NH | 3-CH₃ | 4-CF₃ | |
| 1.542 | NH | 3-CH₃ | 2-OCF₃ | |
| 1.543 | NH | 3-CH₃ | 3-OCF₃ | |
| 1.544 | NH | 3-CH₃ | 4-OCF₃ | |
| 1.545 | NH | 3-CH₃ | 2,3-Cl₂ | |
| 1.546 | NH | 3-CH₃ | 2,4-Cl₂ | |
| 1.547 | NH | 3-CH₃ | 2,5-Cl₂ | |
| 1.548 | NH | 3-CH₃ | 2,6-Cl₂ | |
| 1.549 | NH | 3-CH₃ | 3,4-Cl₂ | |
| 1.550 | NH | 3-CH₃ | 3,5-Cl₂ | |
| 1.551 | NH | 4-CH₃ | H | |
| 1.552 | NH | 4-CH₃ | 2-CH₃ | |
| 1.553 | NH | 4-CH₃ | 3-CH₃ | |
| 1.554 | NH | 4-CH₃ | 4-CH₃ | |
| 1.555 | NH | 4-CH₃ | 2-F | |
| 1.556 | NH | 4-CH₃ | 3-F | |
| 1.557 | NH | 4-CH₃ | 4-F | |
| 1.558 | NH | 4-CH₃ | 2-Cl | |
| 1.559 | NH | 4-CH₃ | 3-Cl | |
| 1.560 | NH | 4-CH₃ | 4-Cl | |
| 1.561 | NH | 4-CH₃ | 2-CF₃ | |
| 1.562 | NH | 4-CH₃ | 3-CF₃ | |
| 1.563 | NH | 4-CH₃ | 4-CF₃ | |
| 1.564 | NH | 4-CH₃ | 2-OCF₃ | |
| 1.565 | NH | 4-CH₃ | 3-OCF₃ | |
| 1.566 | NH | 4-CH₃ | 4-OCF₃ | |
| 1.567 | NH | 4-CH₃ | 2,3-Cl₂ | |
| 1.568 | NH | 4-CH₃ | 2,4-Cl₂ | |
| 1.569 | NH | 4-CH₃ | 2,5-Cl₂ | |
| 1.570 | NH | 4-CH₃ | 2,6-Cl₂ | |
| 1.571 | NH | 4-CH₃ | 3,4-Cl₂ | |
| 1.572 | NH | 4-CH₃ | 3,5-Cl₂ | |
| 1.573 | NH | 2-F | H | |
| 1.574 | NH | 2-F | 2-CH₃ | |
| 1.575 | NH | 2-F | 3-CH₃ | |
| 1.576 | NH | 2-F | 4-CH₃ | |
| 1.577 | NH | 2-F | 2-F | |
| 1.578 | NH | 2-F | 3-F | |
| 1.579 | NH | 2-F | 4-F | |
| 1.580 | NH | 2-F | 2-Cl | |
| 1.581 | NH | 2-F | 3-Cl | |
| 1.582 | NH | 2-F | 4-Cl | |
| 1.583 | NH | 2-F | 2-CF₃ | |
| 1.584 | NH | 2-F | 3-CF₃ | |
| 1.585 | NH | 2-F | 4-CF₃ | |
| 1.586 | NH | 2-F | 2-OCF₃ | |
| 1.587 | NH | 2-F | 3-OCF₃ | |
| 1.588 | NH | 2-F | 4-OCF₃ | |
| 1.589 | NH | 2-F | 2,3-Cl₂ | |
| 1.590 | NH | 2-F | 2,4-Cl₂ | |
| 1.591 | NH | 2-F | 2,5-Cl₂ | |
| 1.592 | NH | 2-F | 2,6-Cl₂ | |
| 1.593 | NH | 2-F | 3,4-Cl₂ | |
| 1.594 | NH | 2-F | 3,5-Cl₂ | |
| 1.595 | NH | 3-F | H | |
| 1.596 | NH | 3-F | 2-CH₃ | |
| 1.597 | NH | 3-F | 3-CH₃ | |
| 1.598 | NH | 3-F | 4-CH₃ | |
| 1.599 | NH | 3-F | 2-F | |
| 1.600 | NH | 3-F | 3-F | |
| 1.601 | NH | 3-F | 4-F | |
| 1.602 | NH | 3-F | 2-Cl | |
| 1.603 | NH | 3-F | 3-Cl | |
| 1.604 | NH | 3-F | 4-Cl | |
| 1.605 | NH | 3-F | 2-CF₃ | |
| 1.606 | NH | 3-F | 3-CF₃ | |
| 1.607 | NH | 3-F | 4-CF₃ | |
| 1.608 | NH | 3-F | 2-OCF₃ | |
| 1.609 | NH | 3-F | 3-OCF₃ | |
| 1.610 | NH | 3-F | 4-OCF₃ | |
| 1.611 | NH | 3-F | 2,3-Cl₂ | |
| 1.612 | NH | 3-F | 2,4-Cl₂ | |
| 1.613 | NH | 3-F | 2,5-Cl₂ | |
| 1.614 | NH | 3-F | 2,6-Cl₂ | |
| 1.615 | NH | 3-F | 3,4-Cl₂ | |
| 1.616 | NH | 3-F | 3,5-Cl₂ | |
| 1.617 | NH | 4-F | H | |
| 1.618 | NH | 4-F | 2-CH₃ | |
| 1.619 | NH | 4-F | 3-CH₃ | |
| 1.620 | NH | 4-F | 4-CH₃ | |
| 1.621 | NH | 4-F | 2-F | |
| 1.622 | NH | 4-F | 3-F | |
| 1.623 | NH | 4-F | 4-F | |
| 1.624 | NH | 4-F | 2-Cl | |
| 1.625 | NH | 4-F | 3-Cl | |
| 1.626 | NH | 4-F | 4-Cl | |
| 1.627 | NH | 4-F | 2-CF₃ | |
| 1.628 | NH | 4-F | 3-CF₃ | |
| 1.629 | NH | 4-F | 4-CF₃ | |
| 1.630 | NH | 4-F | 2-OCF₃ | |
| 1.631 | NH | 4-F | 3-OCF₃ | |
| 1.632 | NH | 4-F | 4-OCF₃ | |
| 1.633 | NH | 4-F | 2,3-Cl₂ | |
| 1.634 | NH | 4-F | 2,4-Cl₂ | |
| 1.635 | NH | 4-F | 2,5-Cl₂ | |
| 1.636 | NH | 4-F | 2,6-Cl₂ | |
| 1.637 | NH | 4-F | 3,4-Cl₂ | |
| 1.638 | NH | 4-F | 3,5-Cl₂ | |
| 1.639 | NH | 2-Cl | H | |
| 1.640 | NH | 2-Cl | 2-CH₃ | |
| 1.641 | NH | 2-Cl | 3-CH₃ | |

TABLE 1-continued

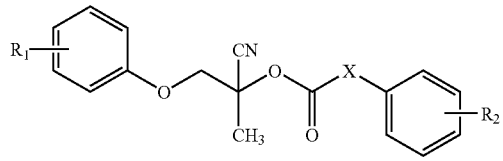

| No. | X | R₁ | R₂ | phys. data |
|---|---|---|---|---|
| 1.642 | NH | 2-Cl | 4-CH₃ | |
| 1.643 | NH | 2-Cl | 2-F | |
| 1.644 | NH | 2-Cl | 3-F | |
| 1.645 | NH | 2-Cl | 4-F | |
| 1.646 | NH | 2-Cl | 2-Cl | |
| 1.647 | NH | 2-Cl | 3-Cl | |
| 1.648 | NH | 2-Cl | 4-Cl | |
| 1.649 | NH | 2-Cl | 2-CF₃ | |
| 1.650 | NH | 2-Cl | 3-CF₃ | |
| 1.651 | NH | 2-Cl | 4-CF₃ | m.p. 142–3° |
| 1.652 | NH | 2-Cl | 2-OCF₃ | |
| 1.653 | NH | 2-Cl | 3-OCF₃ | |
| 1.654 | NH | 2-Cl | 4-OCF₃ | |
| 1.655 | NH | 2-Cl | 2,3-Cl₂ | |
| 1.656 | NH | 2-Cl | 2,4-Cl₂ | |
| 1.657 | NH | 2-Cl | 2,5-Cl₂ | |
| 1.658 | NH | 2-Cl | 2,6-Cl₂ | |
| 1.659 | NH | 2-Cl | 3,4-Cl₂ | |
| 1.660 | NH | 2-Cl | 3,5-Cl₂ | |
| 1.661 | NH | 3-Cl | H | |
| 1.662 | NH | 3-Cl | 2-CH₃ | |
| 1.663 | NH | 3-Cl | 3-CH₃ | |
| 1.664 | NH | 3-Cl | 4-CH₃ | |
| 1.665 | NH | 3-Cl | 2-F | |
| 1.666 | NH | 3-Cl | 3-F | |
| 1.667 | NH | 3-Cl | 4-F | |
| 1.668 | NH | 3-Cl | 2-Cl | |
| 1.669 | NH | 3-Cl | 3-Cl | |
| 1.670 | NH | 3-Cl | 4-Cl | |
| 1.671 | NH | 3-Cl | 2-CF₃ | |
| 1.672 | NH | 3-Cl | 3-CF₃ | |
| 1.673 | NH | 3-Cl | 4-CF₃ | |
| 1.674 | NH | 3-Cl | 2-OCF₃ | |
| 1.675 | NH | 3-Cl | 3-OCF₃ | |
| 1.676 | NH | 3-Cl | 4-OCF₃ | |
| 1.677 | NH | 3-Cl | 2,3-Cl₂ | |
| 1.678 | NH | 3-Cl | 2,4-Cl₂ | |
| 1.679 | NH | 3-Cl | 2,5-Cl₂ | |
| 1.680 | NH | 3-Cl | 2,6-Cl₂ | |
| 1.681 | NH | 3-Cl | 3,4-Cl₂ | |
| 1.682 | NH | 3-Cl | 3,5-Cl₂ | |
| 1.683 | NH | 4-Cl | H | |
| 1.684 | NH | 4-Cl | 2-CH₃ | |
| 1.685 | NH | 4-Cl | 3-CH₃ | |
| 1.686 | NH | 4-Cl | 4-CH₃ | |
| 1.687 | NH | 4-Cl | 2-F | |
| 1.688 | NH | 4-Cl | 3-F | |
| 1.689 | NH | 4-Cl | 4-F | |
| 1.690 | NH | 4-Cl | 2-Cl | |
| 1.691 | NH | 4-Cl | 3-Cl | |
| 1.692 | NH | 4-Cl | 4-Cl | |
| 1.693 | NH | 4-Cl | 2-CF₃ | |
| 1.694 | NH | 4-Cl | 3-CF₃ | |
| 1.695 | NH | 4-Cl | 4-CF₃ | |
| 1.696 | NH | 4-Cl | 2-OCF₃ | |
| 1.697 | NH | 4-Cl | 3-OCF₃ | |
| 1.698 | NH | 4-Cl | 4-OCF₃ | |
| 1.699 | NH | 4-Cl | 2,3-Cl₂ | |
| 1.700 | NH | 4-Cl | 2,4-Cl₂ | |
| 1.701 | NH | 4-Cl | 2,5-Cl₂ | |
| 1.702 | NH | 4-Cl | 2,6-Cl₂ | |
| 1.703 | NH | 4-Cl | 3,4-Cl₂ | |
| 1.704 | NH | 4-Cl | 3,5-Cl₂ | |
| 1.705 | NH | 2-CF₃ | H | |
| 1.706 | NH | 2-CF₃ | 2-CH₃ | |
| 1.707 | NH | 2-CF₃ | 3-CH₃ | |
| 1.708 | NH | 2-CF₃ | 4-CH₃ | |
| 1.709 | NH | 2-CF₃ | 2-F | |

TABLE 1-continued

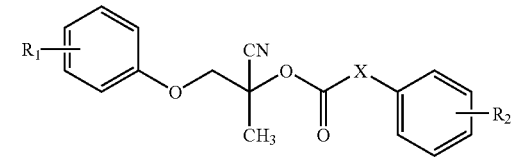

| No. | X | R₁ | R₂ | phys. data |
|---|---|---|---|---|
| 1.710 | NH | 2-CF₃ | 3-F | |
| 1.711 | NH | 2-CF₃ | 4-F | |
| 1.712 | NH | 2-CF₃ | 2-Cl | |
| 1.713 | NH | 2-CF₃ | 3-Cl | |
| 1.714 | NH | 2-CF₃ | 4-Cl | |
| 1.715 | NH | 2-CF₃ | 2-CF₃ | |
| 1.716 | NH | 2-CF₃ | 3-CF₃ | |
| 1.717 | NH | 2-CF₃ | 4-CF₃ | m.p. 162–3° |
| 1.718 | NH | 2-CF₃ | 2-OCF₃ | |
| 1.719 | NH | 2-CF₃ | 3-OCF₃ | |
| 1.720 | NH | 2-CF₃ | 4-OCF₃ | m.p. 119–20° |
| 1.721 | NH | 2-CF₃ | 2,3-Cl₂ | |
| 1.722 | NH | 2-CF₃ | 2,4-Cl₂ | |
| 1.723 | NH | 2-CF₃ | 2,5-Cl₂ | |
| 1.724 | NH | 2-CF₃ | 2,6-Cl₂ | |
| 1.725 | NH | 2-CF₃ | 3,4-Cl₂ | |
| 1.726 | NH | 2-CF₃ | 3,5-Cl₂ | |
| 1.727 | NH | 3-CF₃ | H | |
| 1.728 | NH | 3-CF₃ | 2-CH₃ | |
| 1.729 | NH | 3-CF₃ | 3-CH₃ | |
| 1.730 | NH | 3-CF₃ | 4-CH₃ | |
| 1.731 | NH | 3-CF₃ | 2-F | |
| 1.732 | NH | 3-CF₃ | 3-F | |
| 1.733 | NH | 3-CF₃ | 4-F | |
| 1.734 | NH | 3-CF₃ | 2-Cl | |
| 1.735 | NH | 3-CF₃ | 3-Cl | |
| 1.736 | NH | 3-CF₃ | 4-Cl | |
| 1.737 | NH | 3-CF₃ | 2-CF₃ | |
| 1.738 | NH | 3-CF₃ | 3-CF₃ | |
| 1.739 | NH | 3-CF₃ | 4-CF₃ | |
| 1.740 | NH | 3-CF₃ | 2-OCF₃ | |
| 1.741 | NH | 3-CF₃ | 3-OCF₃ | |
| 1.742 | NH | 3-CF₃ | 4-OCF₃ | |
| 1.743 | NH | 3-CF₃ | 2,3-Cl₂ | |
| 1.744 | NH | 3-CF₃ | 2,4-Cl₂ | |
| 1.745 | NH | 3-CF₃ | 2,5-Cl₂ | |
| 1.746 | NH | 3-CF₃ | 2,6-Cl₂ | |
| 1.747 | NH | 3-CF₃ | 3,4-Cl₂ | |
| 1.748 | NH | 3-CF₃ | 3,5-Cl₂ | |
| 1.749 | NH | 4-CF₃ | H | |
| 1.750 | NH | 4-CF₃ | 2-CH₃ | |
| 1.751 | NH | 4-CF₃ | 3-CH₃ | |
| 1.752 | NH | 4-CF₃ | 4-CH₃ | |
| 1.753 | NH | 4-CF₃ | 2-F | |
| 1.754 | NH | 4-CF₃ | 3-F | |
| 1.755 | NH | 4-CF₃ | 4-F | |
| 1.756 | NH | 4-CF₃ | 2-Cl | |
| 1.757 | NH | 4-CF₃ | 3-Cl | |
| 1.758 | NH | 4-CF₃ | 4-Cl | |
| 1.759 | NH | 4-CF₃ | 2-CF₃ | |
| 1.760 | NH | 4-CF₃ | 3-CF₃ | |
| 1.761 | NH | 4-CF₃ | 4-CF₃ | |
| 1.762 | NH | 4-CF₃ | 2-OCF₃ | |
| 1.763 | NH | 4-CF₃ | 3-OCF₃ | |
| 1.764 | NH | 4-CF₃ | 4-OCF₃ | |
| 1.765 | NH | 4-CF₃ | 2,3-Cl₂ | |
| 1.766 | NH | 4-CF₃ | 2,4-Cl₂ | |
| 1.767 | NH | 4-CF₃ | 2,5-Cl₂ | |
| 1.768 | NH | 4-CF₃ | 2,6-Cl₂ | |
| 1.769 | NH | 4-CF₃ | 3,4-Cl₂ | |
| 1.770 | NH | 4-CF₃ | 3,5-Cl₂ | |
| 1.771 | NH | 2-OCF₃ | H | |
| 1.772 | NH | 2-OCF₃ | 2-CH₃ | |
| 1.773 | NH | 2-OCF₃ | 3-CH₃ | |
| 1.774 | NH | 2-OCF₃ | 4-CH₃ | |
| 1.775 | NH | 2-OCF₃ | 2-F | |
| 1.776 | NH | 2-OCF₃ | 3-F | |
| 1.777 | NH | 2-OCF₃ | 4-F | |

TABLE 1-continued

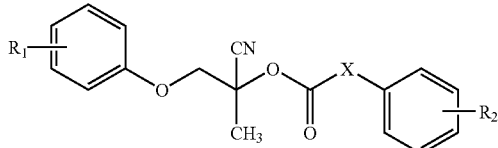

| No. | X | R₁ | R₂ | phys. data |
|---|---|---|---|---|
| 1.778 | NH | 2-OCF₃ | 2-Cl | |
| 1.779 | NH | 2-OCF₃ | 3-Cl | |
| 1.780 | NH | 2-OCF₃ | 4-Cl | |
| 1.781 | NH | 2-OCF₃ | 2-CF₃ | |
| 1.782 | NH | 2-OCF₃ | 3-CF₃ | |
| 1.783 | NH | 2-OCF₃ | 4-CF₃ | |
| 1.784 | NH | 2-OCF₃ | 2-OCF₃ | |
| 1.785 | NH | 2-OCF₃ | 3-OCF₃ | |
| 1.786 | NH | 2-OCF₃ | 4-OCF₃ | |
| 1.787 | NH | 2-OCF₃ | 2,3-Cl₂ | |
| 1.788 | NH | 2-OCF₃ | 2,4-Cl₂ | |
| 1.789 | NH | 2-OCF₃ | 2,5-Cl₂ | |
| 1.790 | NH | 2-OCF₃ | 2,6-Cl₂ | |
| 1.791 | NH | 2-OCF₃ | 3,4-Cl₂ | |
| 1.792 | NH | 2-OCF₃ | 3,5-Cl₂ | |
| 1.793 | NH | 3-OCF₃ | H | |
| 1.794 | NH | 3-OCF₃ | 2-CH₃ | |
| 1.795 | NH | 3-OCF₃ | 3-CH₃ | |
| 1.796 | NH | 3-OCF₃ | 4-CH₃ | |
| 1.797 | NH | 3-OCF₃ | 2-F | |
| 1.798 | NH | 3-OCF₃ | 3-F | |
| 1.799 | NH | 3-OCF₃ | 4-F | |
| 1.800 | NH | 3-OCF₃ | 2-Cl | |
| 1.801 | NH | 3-OCF₃ | 3-Cl | |
| 1.802 | NH | 3-OCF₃ | 4-Cl | |
| 1.803 | NH | 3-OCF₃ | 2-CF₃ | |
| 1.804 | NH | 3-OCF₃ | 3-CF₃ | |
| 1.805 | NH | 3-OCF₃ | 4-CF₃ | |
| 1.806 | NH | 3-OCF₃ | 2-OCF₃ | |
| 1.807 | NH | 3-OCF₃ | 3-OCF₃ | |
| 1.808 | NH | 3-OCF₃ | 4-OCF₃ | |
| 1.809 | NH | 3-OCF₃ | 2,3-Cl₂ | |
| 1.810 | NH | 3-OCF₃ | 2,4-Cl₂ | |
| 1.811 | NH | 3-OCF₃ | 2,5-Cl₂ | |
| 1.812 | NH | 3-OCF₃ | 2,6-Cl₂ | |
| 1.813 | NH | 3-OCF₃ | 3,4-Cl₂ | |
| 1.814 | NH | 3-OCF₃ | 3,5-Cl₂ | |
| 1.815 | NH | 4-OCF₃ | H | |
| 1.816 | NH | 4-OCF₃ | 2-CH₃ | |
| 1.817 | NH | 4-OCF₃ | 3-CH₃ | |
| 1.818 | NH | 4-OCF₃ | 4-CH₃ | |
| 1.819 | NH | 4-OCF₃ | 2-F | |
| 1.820 | NH | 4-OCF₃ | 3-F | |
| 1.821 | NH | 4-OCF₃ | 4-F | |
| 1.822 | NH | 4-OCF₃ | 2-Cl | |
| 1.823 | NH | 4-OCF₃ | 3-Cl | |
| 1.824 | NH | 4-OCF₃ | 4-Cl | |
| 1.825 | NH | 4-OCF₃ | 2-CF₃ | |
| 1.826 | NH | 4-OCF₃ | 3-CF₃ | |
| 1.827 | NH | 4-OCF₃ | 4-CF₃ | |
| 1.828 | NH | 4-OCF₃ | 2-OCF₃ | |
| 1.829 | NH | 4-OCF₃ | 3-OCF₃ | |
| 1.830 | NH | 4-OCF₃ | 4-OCF₃ | |
| 1.831 | NH | 4-OCF₃ | 2,3-Cl₂ | |
| 1.832 | NH | 4-OCF₃ | 2,4-Cl₂ | |
| 1.833 | NH | 4-OCF₃ | 2,5-Cl₂ | |
| 1.834 | NH | 4-OCF₃ | 2,6-Cl₂ | |
| 1.835 | NH | 4-OCF₃ | 3,4-Cl₂ | |
| 1.836 | NH | 4-OCF₃ | 3,5-Cl₂ | |
| 1.837 | NH | 2,3-Cl₂ | H | |
| 1.838 | NH | 2,3-Cl₂ | 2-CH₃ | |
| 1.839 | NH | 2,3-Cl₂ | 3-CH₃ | |
| 1.840 | NH | 2,3-Cl₂ | 4-CH₃ | |
| 1.841 | NH | 2,3-Cl₂ | 2-F | |
| 1.842 | NH | 2,3-Cl₂ | 3-F | |
| 1.843 | NH | 2,3-Cl₂ | 4-F | |
| 1.844 | NH | 2,3-Cl₂ | 2-Cl | |
| 1.845 | NH | 2,3-Cl₂ | 3-Cl | |

TABLE 1-continued

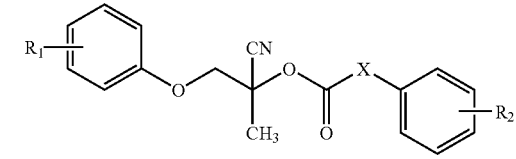

| No. | X | R₁ | R₂ | phys. data |
|---|---|---|---|---|
| 1.846 | NH | 2,3-Cl₂ | 4-Cl | |
| 1.847 | NH | 2,3-Cl₂ | 2-CF₃ | |
| 1.848 | NH | 2,3-Cl₂ | 3-CF₃ | |
| 1.849 | NH | 2,3-Cl₂ | 4-CF₃ | |
| 1.850 | NH | 2,3-Cl₂ | 2-OCF₃ | |
| 1.851 | NH | 2,3-Cl₂ | 3-OCF₃ | |
| 1.852 | NH | 2,3-Cl₂ | 4-OCF₃ | |
| 1.853 | NH | 2,3-Cl₂ | 2,3-Cl₂ | |
| 1.854 | NH | 2,3-Cl₂ | 2,4-Cl₂ | |
| 1.855 | NH | 2,3-Cl₂ | 2,5-Cl₂ | |
| 1.856 | NH | 2,3-Cl₂ | 2,6-Cl₂ | |
| 1.857 | NH | 2,3-Cl₂ | 3,4-Cl₂ | |
| 1.858 | NH | 2,3-Cl₂ | 3,5-Cl₂ | |
| 1.859 | NH | 2,4-Cl₂ | H | |
| 1.860 | NH | 2,4-Cl₂ | 2-CH₃ | |
| 1.861 | NH | 2,4-Cl₂ | 3-CH₃ | |
| 1.862 | NH | 2,4-Cl₂ | 4-CH₃ | |
| 1.863 | NH | 2,4-Cl₂ | 2-F | |
| 1.864 | NH | 2,4-Cl₂ | 3-F | |
| 1.865 | NH | 2,4-Cl₂ | 4-F | |
| 1.866 | NH | 2,4-Cl₂ | 2-Cl | |
| 1.867 | NH | 2,4-Cl₂ | 3-Cl | |
| 1.868 | NH | 2,4-Cl₂ | 4-Cl | |
| 1.869 | NH | 2,4-Cl₂ | 2-CF₃ | |
| 1.870 | NH | 2,4-Cl₂ | 3-CF₃ | |
| 1.871 | NH | 2,4-Cl₂ | 4-CF₃ | |
| 1.872 | NH | 2,4-Cl₂ | 2-OCF₃ | |
| 1.873 | NH | 2,4-Cl₂ | 3-OCF₃ | |
| 1.874 | NH | 2,4-Cl₂ | 4-OCF₃ | |
| 1.875 | NH | 2,4-Cl₂ | 2,3-Cl₂ | |
| 1.876 | NH | 2,4-Cl₂ | 2,4-Cl₂ | |
| 1.877 | NH | 2,4-Cl₂ | 2,5-Cl₂ | |
| 1.878 | NH | 2,4-Cl₂ | 2,6-Cl₂ | |
| 1.879 | NH | 2,4-Cl₂ | 3,4-Cl₂ | |
| 1.880 | NH | 2,4-Cl₂ | 3,5-Cl₂ | |
| 1.881 | NH | 2,5-Cl₂ | H | |
| 1.882 | NH | 2,5-Cl₂ | 2-CH₃ | |
| 1.883 | NH | 2,5-Cl₂ | 3-CH₃ | |
| 1.884 | NH | 2,5-Cl₂ | 4-CH₃ | |
| 1.885 | NH | 2,5-Cl₂ | 2-F | |
| 1.886 | NH | 2,5-Cl₂ | 3-F | |
| 1.887 | NH | 2,5-Cl₂ | 4-F | |
| 1.888 | NH | 2,5-Cl₂ | 2-Cl | |
| 1.889 | NH | 2,5-Cl₂ | 3-Cl | |
| 1.890 | NH | 2,5-Cl₂ | 4-Cl | |
| 1.891 | NH | 2,5-Cl₂ | 2-CF₃ | |
| 1.892 | NH | 2,5-Cl₂ | 3-CF₃ | |
| 1.893 | NH | 2,5-Cl₂ | 4-CF₃ | |
| 1.894 | NH | 2,5-Cl₂ | 2-OCF₃ | |
| 1.895 | NH | 2,5-Cl₂ | 3-OCF₃ | |
| 1.896 | NH | 2,5-Cl₂ | 4-OCF₃ | |
| 1.897 | NH | 2,5-Cl₂ | 2,3-Cl₂ | |
| 1.898 | NH | 2,5-Cl₂ | 2,4-Cl₂ | |
| 1.899 | NH | 2,5-Cl₂ | 2,5-Cl₂ | |
| 1.900 | NH | 2,5-Cl₂ | 2,6-Cl₂ | |
| 1.901 | NH | 2,5-Cl₂ | 3,4-Cl₂ | |
| 1.902 | NH | 2,5-Cl₂ | 3,5-Cl₂ | |
| 1.903 | NH | 2,6-Cl₂ | H | |
| 1.904 | NH | 2,6-Cl₂ | 2-CH₃ | |
| 1.905 | NH | 2,6-Cl₂ | 3-CH₃ | |
| 1.906 | NH | 2,6-Cl₂ | 4-CH₃ | |
| 1.907 | NH | 2,6-Cl₂ | 2-F | |
| 1.908 | NH | 2,6-Cl₂ | 3-F | |
| 1.909 | NH | 2,6-Cl₂ | 4-F | |
| 1.910 | NH | 2,6-Cl₂ | 2-Cl | |
| 1.911 | NH | 2,6-Cl₂ | 3-Cl | |
| 1.912 | NH | 2,6-Cl₂ | 4-Cl | |
| 1.913 | NH | 2,6-Cl₂ | 2-CF₃ | |

TABLE 1-continued

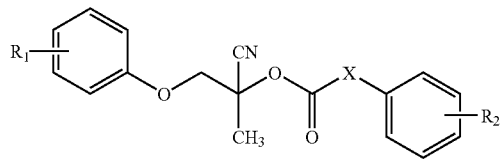

| No. | X | R$_1$ | R$_2$ | phys. data |
|---|---|---|---|---|
| 1.914 | NH | 2,6-Cl$_2$ | 3-CF$_3$ | |
| 1.915 | NH | 2,6-Cl$_2$ | 4-CF$_3$ | |
| 1.916 | NH | 2,6-Cl$_2$ | 2-OCF$_3$ | |
| 1.917 | NH | 2,6-Cl$_2$ | 3-OCF$_3$ | |
| 1.918 | NH | 2,6-Cl$_2$ | 4-OCF$_3$ | |
| 1.919 | NH | 2,6-Cl$_2$ | 2,3-Cl$_2$ | |
| 1.920 | NH | 2,6-Cl$_2$ | 2,4-Cl$_2$ | |
| 1.921 | NH | 2,6-Cl$_2$ | 2,5-Cl$_2$ | |
| 1.922 | NH | 2,6-Cl$_2$ | 2,6-Cl$_2$ | |
| 1.923 | NH | 2,6-Cl$_2$ | 3,4-Cl$_2$ | |
| 1.924 | NH | 2,6-Cl$_2$ | 3,5-Cl$_2$ | |
| 1.925 | NH | 3,4-Cl$_2$ | H | |
| 1.926 | NH | 3,4-Cl$_2$ | 2-CH$_3$ | |
| 1.927 | NH | 3,4-Cl$_2$ | 3-CH$_3$ | |
| 1.928 | NH | 3,4-Cl$_2$ | 4-CH$_3$ | |
| 1.929 | NH | 3,4-Cl$_2$ | 2-F | |
| 1.930 | NH | 3,4-Cl$_2$ | 3-F | |
| 1.931 | NH | 3,4-Cl$_2$ | 4-F | |
| 1.932 | NH | 3,4-Cl$_2$ | 2-Cl | |
| 1.933 | NH | 3,4-Cl$_2$ | 3-Cl | |
| 1.934 | NH | 3,4-Cl$_2$ | 4-Cl | |
| 1.935 | NH | 3,4-Cl$_2$ | 2-CF$_3$ | |
| 1.936 | NH | 3,4-Cl$_2$ | 3-CF$_3$ | |
| 1.937 | NH | 3,4-Cl$_2$ | 4-CF$_3$ | |
| 1.938 | NH | 3,4-Cl$_2$ | 2-OCF$_3$ | |
| 1.939 | NH | 3,4-Cl$_2$ | 3-OCF$_3$ | |
| 1.940 | NH | 3,4-Cl$_2$ | 4-OCF$_3$ | |
| 1.941 | NH | 3,4-Cl$_2$ | 2,3-Cl$_2$ | |
| 1.942 | NH | 3,4-Cl$_2$ | 2,4-Cl$_2$ | |
| 1.943 | NH | 3,4-Cl$_2$ | 2,5-Cl$_2$ | |
| 1.944 | NH | 3,4-Cl$_2$ | 2,6-Cl$_2$ | |
| 1.945 | NH | 3,4-Cl$_2$ | 3,4-Cl$_2$ | |
| 1.946 | NH | 3,4-Cl$_2$ | 3,5-Cl$_2$ | |
| 1.947 | NH | 3,5-Cl$_2$ | H | |
| 1.948 | NH | 3,5-Cl$_2$ | 2-CH$_3$ | |
| 1.949 | NH | 3,5-Cl$_2$ | 3-CH$_3$ | |
| 1.950 | NH | 3,5-Cl$_2$ | 4-CH$_3$ | |
| 1.951 | NH | 3,5-Cl$_2$ | 2-F | |
| 1.952 | NH | 3,5-Cl$_2$ | 3-F | |
| 1.953 | NH | 3,5-Cl$_2$ | 4-F | |
| 1.954 | NH | 3,5-Cl$_2$ | 2-Cl | |
| 1.955 | NH | 3,5-Cl$_2$ | 3-Cl | |
| 1.956 | NH | 3,5-Cl$_2$ | 4-Cl | |
| 1.957 | NH | 3,5-Cl$_2$ | 2-CF$_3$ | |
| 1.958 | NH | 3,5-Cl$_2$ | 3-CF$_3$ | |
| 1.959 | NH | 3,5-Cl$_2$ | 4-CF$_3$ | |
| 1.960 | NH | 3,5-Cl$_2$ | 2-OCF$_3$ | |
| 1.961 | NH | 3,5-Cl$_2$ | 3-OCF$_3$ | |
| 1.962 | NH | 3,5-Cl$_2$ | 4-OCF$_3$ | |
| 1.963 | NH | 3,5-Cl$_2$ | 2,3-Cl$_2$ | |
| 1.964 | NH | 3,5-Cl$_2$ | 2,4-Cl$_2$ | |
| 1.965 | NH | 3,5-Cl$_2$ | 2,5-Cl$_2$ | |
| 1.966 | NH | 3,5-Cl$_2$ | 2,6-Cl$_2$ | |
| 1.967 | NH | 3,5-Cl$_2$ | 3,4-Cl$_2$ | |
| 1.968 | NH | 3,5-Cl$_2$ | 3,5-Cl$_2$ | |

Biological Examples

1. In-Vivo Test on *Trichostrongylus colubriformis* and *Haemonchus contortus* on *Mongolian gerbils* (*Meriones unguiculatus*) Using Peroral Application Six to eight week old Mongolian gerbils are infected by artificial feeding with ca. 2000 third instar larvae each of *T. colubriformis* and *H. contortus*. 6 days after infection, the gerbils are lightly anaesthetised with N$_2$O and treated by peroral application with the test compounds, dissolved in a mixture of 2 parts DMSO and 1 part polyethylene glycol (PEG 300), in quantities of 100, 32 and 10–0.1 mg/kg. On day 9 (3 days after treatment), when most of the *H. contortus* that are still present are late 4th instar larvae and most of the *T. colubriformis* are immature adults, the gerbils are killed in order to count the worms. The efficacy is calculated as the % reduction of the number of worms in each gerbil, compared with the geometric average of number of worms from 8 infected and untreated gerbils.

In this test, a vast reduction in nematode infestation is achieved with compounds of formula I.

To examine the insecticidal and/or acaricidal activity of the compounds of formula I on animals and plants, the following test methods may be used.

2. Acaricidal Activity on *Boophilus microplus* (Biarra Strain)

A piece of sticky tape is attached horizontally to a PVC sheet, so that 10 fully engorged female ticks of *Boophilus microplus* (Biarra strain) can be adhered thereto by their backs, side by side, in a row. Using an injection needle, 1 µl of a liquid is injected into each tick. The liquid is a 1:1 mixture of polyethylene glycol and acetone and it contains, dissolved therein, a certain amount of active ingredient chosen from 1, 0.1 or 0.01 µg per tick. Control animals are given an injection without active ingredient. After treatment, the animals are kept under normal conditions in an insectarium at ca. 28° C. and at 80% relative humidity until oviposition takes place and the larvae have hatched from the eggs of the control animals. The activity of a tested substance is determined by IR$_{90}$, i.e. an evaluation is made of the dosage of active ingredient at which 9 out of 10 female ticks (=90%) lay eggs that are infertile even after 30 days.

3. In Vitro Efficacy on Engorged Female *Boophilus microplus* (BIARRA)

4×10 engorged female ticks of the OP-resistant BIARRA strain are adhered to a sticky strip and covered for 1 hour with a cotton-wool ball soaked in an emulsion or suspension of the test compound in concentrations of 500, 125, 31 and 8 ppm respectively. Evaluation takes place 28 days later based on mortality, oviposition and hatched larvae.

An indication of the activity of the test compounds is shown by the number of females that
  die quickly before laying eggs,
  survive for some time without laying eggs,
  lay eggs in which no embryos are formed,
  lay eggs in which embryos form, from which no larvae hatch, and
  lay eggs in which embryos form, from which larvae normally hatch within 26 to 27 days.

4. In Vitro Efficacy on Nymphs of *Amblyomma hebraeum*

About 5 fasting nymphs are placed in a polystyrene test tube containing 2 ml of the test compound in solution, suspension or emulsion.

After immersion for 10 minutes, and shaking for 2×10 seconds on a vortex mixer, the test tubes are blocked up with a tight wad of cotton wool and rotated. As soon as all the liquid has been soaked up by the cotton wool ball, it is pushed half-way into the test tube which is still being rotated, so that most of the liquid is squeezed out of the cotton-wool ball and flows into a Petri dish below.

The test tubes are then kept at room temperature in a room with daylight until evaluated. After 14 days, the test tubes are immersed in a beaker of boiling water. If the ticks begin to move in reaction to the heat, the test substance is inactive at the tested concentration, otherwise the ticks are regarded as dead and the test substances regarded as active at the tested concentration. All substances are tested in a concentration range of 0.1 to 100 ppm.

5. Activity Against *Dermanyssus callinae*

2 to 3 ml of a solution containing 10 ppm active ingredient, and ca. 200 mites (*Dermanyssus gallinae*) at different stages of development are added to a glass container which is open at the top. Then the container is closed with a wad of cotton wool, shaken for 10 minutes until the mites are completely wet, and then inverted briefly so that the remaining test solution can be absorbed by the cotton wool. After 3 days, the mortality of the mites is determined by counting the dead individuals and indicated as a percentage.

6. Activity Against *Musca domestica*

A sugar cube is treated with a solution of the test substance in such a way that the concentration of test substance in the sugar, after drying over night, is 250 ppm. The cube treated in this way is placed on an aluminium dish with wet cotton wool and 10 adult *Musca domestica* of an OP-resistant strain, covered with a beaker and incubated at 25° C. The mortality rate is determined after 24 hours.

We claim:

1. A compound of formula (I)

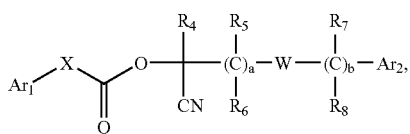

wherein
Ar$_1$ and Ar$_2$, independently of one another, signify unsubstituted phenyl or phenyl which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_2$–C$_6$-alkenyl, halo-C$_2$–C$_6$-alkenyl, C$_2$–C$_6$-alkinyl, C$_3$–C$_6$-cycloalkyl, C$_2$–C$_6$-alkenyloxy, halo-C$_2$–C$_6$-alkenyloxy, C$_1$–C$_6$-alkylthio, halo-C$_1$–C$_6$-alkylthio, C$_1$–C$_6$-alkylsulfonyloxy, halo-C$_1$–C$_6$-alkylsulfonyloxy, C$_1$–C$_6$-alkylsulfinyl, halo-C$_1$–C$_6$-alkylsulfinyl, C$_1$–C$_6$-alkylsulfonyl, halo-C$_1$–C$_6$-alkylsulfonyl, C$_2$–C$_6$-alkenylthio, halo-C$_2$–C$_6$-alkenylthio, C$_2$–C$_6$-alkenylsulfinyl, halo-C$_2$–C$_6$-alkenylsulfinyl, C$_2$–C$_6$-alkenylsulfonyl, halo-C$_2$–C$_6$-alkenylsulfonyl, C$_1$–C$_6$-alkylamino, di-C$_1$–C$_6$-alkylamino, C$_1$–C$_6$-alkylsulfonylamino, halo-C$_1$–C$_6$-alkylsulfonylamino, C$_1$–C$_6$-alkylcarbonyl, halo-C$_1$–C$_6$-alkylcarbonyl, C$_1$–C$_6$-alkoxycarbonyl, C$_1$–C$_6$-alkylaminocarbonyl, di-C$_1$–C$_6$-alkylaminocarbonyl; unsubstituted phenylamino or phenylamino which is substituted once or many times; unsubstituted phenylcarbonyl or phenylcarbonyl which is substituted once or many times; unsubstituted phenyl or phenyl which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_1$–C$_6$-alkylsulfonyl and halo-C$_1$–C$_6$-alkylsulfonyl; unsubstituted phenoxy or phenoxy which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_1$–C$_6$-alkylsulfonyl and halo-C$_1$–C$_6$-alkylsulfonyl; unsubstituted phenylacetylenyl or phenylacetylenyl which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_1$–C$_6$-alkylsulfonyl and halo-C$_1$–C$_6$-alkylsulfonyl; and unsubstituted pyridyloxy or pyridyloxy which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_1$–C$_6$-alkylsulfonyl and halo-C$_1$–C$_6$-alkylsulfonyl; halo-C$_2$–C$_6$-alkenylsulfinyl, C$_1$–C$_6$-alkylsulfonyl and halo-C$_1$–C$_6$-alkylsulfonyl, R$_4$, R$_5$, R$_6$, R$_7$ and R$_8$ are either, independently of one another, hydrogen, halogen, unsubstituted C$_1$–C$_6$-alkyl or C$_1$–C$_6$-alkyl which is substituted once or many times, unsubstituted C$_2$–C$_6$-alkenyl or C$_2$–C$_6$-alkenyl which is substituted once or many times, unsubstituted C$_2$–C$_6$-alkinyl or C$_2$–C$_6$-alkinyl which is substituted once or many times, whereby the substituents may each be independent of one another and are selected from the group consisting of halogen, C$_1$–C$_6$-alkoxy and halo-C$_1$–C$_6$-alkoxy; C$_3$–C$_6$-cycloalkyl, whereby the substituents may be independent of one another and are selected from the group consisting of halogen and C$_1$–C$_6$-alkyl; unsubstituted phenyl or phenyl which is substituted once or many times, whereby the substituents may be independent of one another and are selected from the group consisting of halogen, nitro, cyano, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkylthio, halo-C$_1$–C$_6$-alkylthio, C$_1$–C$_6$-alkylsulfinyl, halo-C$_1$–C$_6$-alkylsulfinyl, C$_1$–C$_6$-alkylsulfonyl, halo-C$_1$–C$_6$-alkylsulfonyl, C$_1$–C$_6$-alkylamino or di-C$_1$–C$_6$-alkylamino;

or R$_4$ and R$_5$ together signify C$_2$–C$_6$-alkylene;
W signifies O, S, S(O$_2$) or N(R$_9$);
R$_9$ signifies hydrogen or C$_1$–C$_6$-alkyl;
X signifies O, S or N(R$_{10}$);
R$_{10}$ signifies hydrogen, C$_1$–C$_6$-alkyl, halo-C$_1$–C$_6$-alkyl, allyl or C$_1$–C$_6$-alkoxymethyl;
a signifies 1, 2, 3 or 4; and
b signifies 0, 1, 2, 3 or 4, whereby said compound is in free form or salt form.

2. A compound of formula (I) according to claim 1, wherein
Ar$_1$ and Ar$_2$, independently of one another, signify unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_2$–$C_6$-alkenyl, halo-$C_2$–$C_6$-alkenyl, $C_2$–$C_6$-alkinyl, $C_3$–$C_6$-cycloalkyl, $C_2$–$C_6$-alkenyloxy, halo-$C_2$–$C_6$-alkenyloxy, $C_1$–$C_6$-alkylthio, halo-$C_1$–$C_6$-alkylthio, $C_1$–$C_6$-alkylamino, di-$C_1$–$C_6$-alkylamino, $C_1$–$C_6$-alkylcarbonyl, halo-$C_1$–$C_6$-alkylcarbonyl, $C_1$–$C_6$-alkoxycarbonyl, $C_1$–$C_6$-alkylaminocarbonyl and di-$C_1$–$C_6$-alkylaminocarbonyl.

3. A compound of formula (I) according to claim 1, wherein
$Ar_1$ and $Ar_2$, independently of one another, signify phenyl that is either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy, halo-$C_1$–$C_6$-alkoxy, $C_3$–$C_6$-cycloalkyl, $C_1$–$C_6$-alkylthio, halo-$C_1$–$C_6$-alkylthio, $C_1$–$C_6$-alkylcarbonyl, halo-$C_1$–$C_6$-alkylcarbonyl, $C_1$–$C_6$-alkoxycarbonyl, $C_1$–$C_6$-alkylaminocarbonyl and di-$C_1$–$C_6$-alkylaminocarbonyl.

4. A compound of formula (I) according to claim 1, wherein
$Ar_1$ and $Ar_2$, independently of one another, signify phenyl that is either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy and halo-$C_1$–$C_6$-alkoxy.

5. A compound of formula (I) according to claim 1, wherein
$R_4$, $R_5$, $R_6$, $R_7$ and $R_8$ are, independently of one another, hydrogen, halogen, unsubstituted $C_1$–$C_6$-alkyl or $C_1$–$C_6$-alkyl which is substituted once or many times, unsubstituted $C_2$–$C_6$-alkenyl or $C_2$–$C_6$-alkenyl which is substituted once or many times, unsubstituted $C_2$–$C_6$-alkinyl or $C_2$–$C_6$-alkinyl which is substituted once or many times, whereby the substituents may each be independent of one another and are selected from the group consisting of halogen, $C_1$–$C_6$-alkoxy and halo-$C_1$–$C_6$-alkoxy; unsubstituted $C_3$–$C_6$-cycloalkyl or $C_3$–$C_6$-cycloalkyl which is substituted once or many times, whereby the substituents may be independent of one another and are selected from the group consisting of halogen and $C_1$–$C_6$-alkyl; or unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkylsulfonyl, halo-$C_1$–$C_6$-alkylsulfonyl, $C_1$–$C_6$-alkylamino or di-$C_1$–$C_6$-alkylamino.

6. A compound of formula (I) according to claim 1, wherein
$R_4$, $R_5$, $R_6$, $R_7$ and $R_8$ are, independently of one another, hydrogen, halogen, unsubstituted $C_1$–$C_6$-alkyl or $C_1$–$C_6$-alkyl which is substituted once or many times, unsubstituted $C_2$–$C_6$-alkenyl or $C_2$–$C_6$-alkenyl which is substituted once or many times, unsubstituted $C_2$–$C_6$-alkinyl or $C_2$–$C_6$-alkinyl which is substituted once or many times, whereby the substituents may each be independent of one another and are selected from the group consisting of halogen and $C_1$–$C_6$-alkoxy; unsubstituted $C_3$–$C_6$-cycloalkyl or $C_3$–$C_6$-cycloalkyl which is substituted once or many times, whereby the substituents may be independent of one another and are selected from the group consisting of halogen and $C_1$–$C_4$-alkyl; or unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy or halo-$C_1$–$C_6$-alkoxy.

7. A compound of formula (I) according to claim 1, wherein $R_4$, $R_5$, $R_6$, $R_7$ and $R_8$ are, independently of one another, hydrogen, halogen, $C_1$–$C_4$-alkyl or halo-$C_1$–$C_4$-alkyl.

8. A compound of formula (I) according to claim 1, wherein W is O, S or $N(R_9)$.

9. A compound of formula (I) according to claim 1, wherein W is O or S.

10. A compound of formula (I) according to claim 1, wherein W is O.

11. A compound of formula (I) according to claim 1, wherein $R_9$ signifies hydrogen or $C_1$-$R_4$-alkyl.

12. A compound of formula (I) according to claim 1, wherein $R_9$ signifies hydrogen or $C_1$–$C_2$-alkyl.

13. A compound of formula (I) according to claim 1, wherein $R_9$ signifies hydrogen.

14. A compound of formula (I) according to claim 1, wherein $R_{10}$ is hydrogen, $C_1$–$C_4$-alkyl or halo-$C_1$–$C_4$-alkyl.

15. A compound of formula (I) according to claim 1, wherein $R_{10}$ is hydrogen or $C_1$–$C_4$-alkyl.

16. A compound of formula (I) according to claim 1, wherein $R_{10}$ is hydrogen.

17. A compound of formula (I) according to claim 1, wherein a signifies 1, 2 or 3.

18. A compound of formula (I) according to claim 1, wherein a signifies 1 or 2.

19. A compound of formula (I) according to claim 1, wherein a signifies 1.

20. A compound of formula (I) according to claim 1, wherein b is 0, 1, 2 or 3.

21. A compound of formula (I) according to claim 1, wherein b is 0 or 1.

22. A compound of formula (I) according to claim 1, wherein b is 0.

23. A compound of formula (I) according to claim 1, wherein
$Ar_1$ and $Ar_2$, independently of one another, signify unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_2$–$C_6$-alkenyl, halo-$C_2$–$C_6$-alkenyl, $C_2$–$C_6$-alkinyl, $C_3$–$C_6$-cycloalkyl, $C_2$–$C_6$-alkenyloxy, halo-$C_2$–$C_6$-alkenyloxy, $C_1$–$C_6$-alkylthio, halo-$C_1$–$C_6$-alkylthio, $C_1$–$C_6$-alkylamino, di-$C_1$–$C_6$-alkylamino, $C_1$–$C_6$-alkylcarbonyl, halo-$C_1$–$C_6$-alkylcarbonyl, $C_1$–$C_6$-alkoxycarbonyl, $C_1$–$C_6$-alkylaminocarbonyl and di-$C_1$–$C_6$-alkylaminocarbonyl;
$R_4$, $R_5$, $R_6$, $R_7$ and $R_8$ are, independently of one another, hydrogen, halogen, unsubstituted $C_1$–$C_6$-alkyl or $C_1$–$C_6$-alkyl which is substituted once or many times, unsubstituted $C_2$–$C_6$-alkenyl or $C_2$–$C_6$-alkenyl which is substituted once or many times, unsubstituted $C_2$–$C_6$-alkinyl or $C_2$–$C_6$-alkinyl which is substituted once or many times, whereby the substituents may each be independent of one another and are selected from the group consisting of halogen and $C_1$–$C_6$-alkoxy; unsubstituted $C_3$–$C_6$-cycloalkyl or $C_3$–$C_6$-cycloalkyl which is substituted once or many times, whereby the substituents may be independent of one another and are selected from the group consisting of halogen and $C_1$–$C_6$-alkyl; or unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkylsulfonyl, halo-$C_1$–$C_6$-alkylsulfonyl, $C_1$–$C_6$-alkylamino or di-$C_1$–$C_6$-alkylamino;

W signifies O, S or N($R_9$);

$R_9$ signifies hydrogen or $C_1$–$C_4$-alkyl;

X signifies N($R_{10}$);

$R_{10}$ signifies hydrogen, $C_1$–$C_4$-alkyl or halo-$C_1$–$C_4$-alkyl;

a signifies 1, 2 or 3;

and b signifies 0, 1, 2 or 3.

24. A compound of formula (I) according to claim 1, wherein $Ar_1$ and $Ar_2$, independently of one another, signify phenyl that is either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy, halo-$C_1$–$C_6$-alkoxy, $C_3$–$C_6$-cycloalkyl, $C_1$–$C_6$-alkylthio, halo-$C_1$–$C_6$-alkylthio, $C_1$–$C_6$-alkylcarbonyl, halo-$C_1$–$C_6$-alkylcarbonyl, $C_1$–$C_6$-alkoxycarbonyl, $C_1$–$C_6$-alkylaminocarbonyl and di-$C_1$–$C_6$-alkylaminocarbonyl;

$R_4$, $R_5$, $R_6$, $R_7$ and $R_8$ are, independently of one another, hydrogen, halogen, unsubstituted $C_1$–$C_6$-alkyl or $C_1$–$C_6$-alkyl which is substituted once or many times, unsubstituted $C_2$–$C_6$-alkenyl or $C_2$–$C_6$-alkenyl which is substituted once or many times, unsubstituted $C_2$–$C_6$-alkinyl or $C_2$–$C_6$-alkinyl which is substituted once or many times, whereby the substituents may each be independent of one another and are selected from the group consisting of halogen and $C_1$–$C_6$-alkoxy; unsubstituted $C_3$–$C_6$-cycloalkyl or $C_3$–$C_6$-cycloalkyl which is substituted once or many times, whereby the substituents may be independent of one another and are selected from the group consisting of halogen and $C_1$–$C_4$-alkyl; or unsubstituted phenyl or phenyl which is substituted once or many times, whereby the substituents may be independent of one another and are selected from the group consisting of halogen, nitro, cyano, $C_1$–$C_6$-alkyl, halo-$C_1$–$C_6$-alkyl, $C_1$–$C_6$-alkoxy or halo-$C_1$–$C_6$-alkoxy;

W is O or S;

$R_9$ signifies hydrogen or $C_1$–$C_2$-alkyl;

X signifies N($R_{10}$);

$R_{10}$ signifies hydrogen or $C_1$–$C_4$-alkyl;

a signifies 1 or 2;

and b signifies 0 or 1.

25. A compound of formula (I) according to claim 1, wherein $Ar_1$ and $Ar_2$, independently of one another, signify phenyl that is either unsubstituted or substituted once or many times, whereby the substituents may be independent of one another and are selected from the group consisting of halogen, $C_1$–$C_6$-alkyl, halo-$C_1$–$C_6$-alkyl, $C_1$–$C_6$-alkoxy and halo-$C_1$–$C_6$-alkoxy;

$R_4$, $R_5$, $R_6$, $R_7$ and $R_8$, independently of one another, signify hydrogen, halogen, $C_1$–$C_4$-alkyl or halo-$C_1$–$C_4$-alkyl;

W signifies O;

$R_9$ signifies hydrogen;

X signifies N($R_{10}$);

$R_{10}$ signifies hydrogen;

a signifies 1; and b is 1.

26. A compound of formula (I) according to claim 1, named 3-(2-chlorophenoxy)-2-hydroxy-2-methylpropionitrile.

27. Composition for the control of parasites comprising at least one compound of formula (I) according to claim 1, in addition to carriers and/or dispersants.

28. A method for controlling parasites comprising applying to said parasites or its habitat a parasiticidal effective amount of at least one compound of formula (I) of claim 1.

29. The method of claim 28 wherein said parasiticidal effective amount of said at least one compound of formula (I) of claim 1 is administered to an animal host of said parasite.

30. The method of claim 29 whereby said at least one compound of formula (I) of claim 1 is administered to said animal host topically, perorally, parenterally, or subcutaneously.

31. The method of claim 28 whereby said compound is in a formulation consisting of the group of pour-on, spot-on, tablet, chewie, powder, boli, capsules, suspension, emulsion, solution, injectable, water-additive, and food-additive.

32. The method of claim 28 wherein said parasites are helminthes.

33. A method of treating an animal for parasites comprising administering to said animal in need of treatment thereof a parasiticidal effective amount of the composition of claim 27.

34. The method of claim 33 wherein said administration to said animal is topically, perorally, parenterally, or subcutaneously.

35. The method of claim 33 wherein said composition of claim 27 is in a formulation consisting of the group of pour-on, spot-on, tablet, chewie, powder, boli, capsules, suspension, emulsion, solution, injectable, water-additive, and food-additive.

36. The method of claim 33 wherein said parasites are helminthes.

37. A method for the preparation of compounds of formula (I) in free form or in salt form, according to claim 1, wherein X is defined as given for formula (I) with the exception of NH, comprising reacting a compound of formula (II)

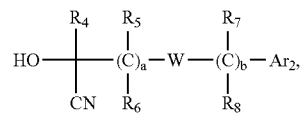

wherein $R_4$, $R_5$, $R_6$, $R_7$, $R_8$, $Ar_2$, W, a and b are defined as given for formula (I), with a compound of formula (III)

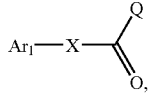   III wherein $Ar_1$ is defined as given for said formula (I), X is defined as given for formula (I) with the exception of NH, and Q is a leaving group, and optionally separating the mixture of isomers.

38. A method for the preparation of compounds of formula (I) in free form or in salt form, according to claim 1, wherein X is NH, comprising reacting optionally in the presence of a basic catalyst a compound of formula (II)

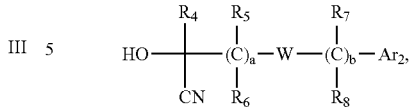   II wherein $R_4$, $R_5$, $R_6$, $R_7$, $R_8$, $Ar_2$, W, a and b are defined as given for formula (I), with a compound of formula (VI)

$Ar_1$—NCO   VI, wherein $Ar_1$ is defined as given for formula (I), and optionally separating the mixture of isomers.

39. A compound of formula (I) according to claim 1, named 4-trifluoromethylphenyl)-carbamic acid-2(2-chlorophenoxy)-1-cyano-1-methyl-ethylester.

* * * * *